(12) United States Patent
Villadsen et al.

(10) Patent No.: US 12,337,157 B2
(45) Date of Patent: Jun. 24, 2025

(54) INJECTION DEVICE FOR DELIVERING A LIQUID DRUG AND A METHOD OF ASSEMBLY

(71) Applicant: Novo Nordisk A/S, Bagsvaerd (DK)

(72) Inventors: Nicolai Michael Villadsen, Oelstykke (DK); Bo Kvolsbjerg, Helsingoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 605 days.

(21) Appl. No.: 17/773,137

(22) PCT Filed: Dec. 9, 2020

(86) PCT No.: PCT/EP2020/085273
§ 371 (c)(1),
(2) Date: Apr. 29, 2022

(87) PCT Pub. No.: WO2021/122221
PCT Pub. Date: Jun. 24, 2021

(65) Prior Publication Data
US 2022/0362483 A1    Nov. 17, 2022

(30) Foreign Application Priority Data
Dec. 18, 2019 (EP) .................................... 19217343

(51) Int. Cl.
*A61M 5/315* (2006.01)
(52) U.S. Cl.
CPC ..... *A61M 5/31585* (2013.01); *A61M 2207/00* (2013.01)

(58) Field of Classification Search
CPC .......... A61M 5/31585; A61M 5/31568; A61M 5/3157
See application file for complete search history.

(56) References Cited

U.S. PATENT DOCUMENTS

| | | | |
|---|---|---|---|
| 8,939,945 B2 | 1/2015 | Veasey et al. | |
| 10,137,252 B2 | 11/2018 | Roervig et al. | |
| 10,143,806 B2 | 12/2018 | Hirschel et al. | |
| 10,245,387 B2 | 4/2019 | Stefanov et al. | |
| 2007/0016143 A1 | 1/2007 | Miller et al. | |
| 2015/0224266 A1* | 8/2015 | Plumptre | A61M 5/31528 604/189 |
| 2016/0051766 A1* | 2/2016 | Marsh | A61M 5/3157 604/207 |
| 2017/0266384 A1* | 9/2017 | Veasey | A61M 5/31553 |
| 2018/0169346 A1 | 6/2018 | Hostettler et al. | |
| 2018/0333534 A1 | 11/2018 | Roervig et al. | |

(Continued)

FOREIGN PATENT DOCUMENTS

| | | |
|---|---|---|
| EP | 1541185 | 6/2005 |
| EP | 2968777 B1 | 5/2019 |

(Continued)

*Primary Examiner* — Dung T Ulsh
(74) *Attorney, Agent, or Firm* — Wesley Nicolas

(57) ABSTRACT

The invention relates to a pre-filled injection device with a non-removable cartridge wherein the drive mechanics comprises a threaded piston rod which is moved helically in a nut secured to a housing structure. During assembly of the injection device it is possible to rotate the nut member to thereby advance the piston rod into a position eliminating any air-gap otherwise occurring between the piston rod and the plunger inside the cartridge.

11 Claims, 15 Drawing Sheets

(56) References Cited

U.S. PATENT DOCUMENTS

2019/0160229 A1* 5/2019 Alagia .................... A61M 5/24
2022/0379041 A1* 12/2022 Matias .............. A61M 5/31568

FOREIGN PATENT DOCUMENTS

| JP | 2007512932 A | 5/2007 |
| JP | 2017518840 A | 7/2017 |
| JP | 2017538549 A | 12/2017 |
| WO | 9938554 | 8/1999 |
| WO | 2005018721 | 3/2005 |
| WO | 2009095332 A1 | 8/2009 |
| WO | 2017001694 A1 | 1/2017 |
| WO | 18002313 A1 | 1/2018 |
| WO | 2018007259 A2 | 1/2018 |
| WO | 2019072826 A1 | 4/2019 |

* cited by examiner

INJECTION DEVICE FOR DELIVERING A LIQUID DRUG AND A METHOD OF ASSEMBLY

CROSS-REFERENCE TO RELATED APPLICATIONS

This application is a 35 U.S.C. § 371 National Stage application of International Application PCT/EP2020/085273 (published as WO 2021/122221), filed Dec. 9, 2020, which claims priority to European Patent Application 19217343.3, filed Dec. 18, 2019; the contents of which are incorporated herein by reference.

THE TECHNICAL FIELD OF THE INVENTION

The present invention relates to a pre-filled injection device for delivering one or preferably more doses of a liquid drug. The present invention especially relates to such injection device wherein the distance occurring between the piston rod moving a plunger inside a cartridge and the plunger itself has been eliminated, or at least significantly reduced prior to delivering the pre-filled injection device to the end-user.

In a second aspect, the present invention relates to a method for assembling a pre-filled injection device having such zero-point adjustment.

DESCRIPTION OF RELATED ART

Injection devices are widely known and used in the treatment of a large variety of different disease and are especially used within the area of diabetes. A very popular type of injection devices are the so-called disposable or prefilled injection devices. This type of injection devices usually contains a cartridge which contains a predetermined amount of liquid drug to be injected and which cartridge is non-replaceable embedded in the injection device. Hence, when the content contained in the encapsulated cartridge is used, the user discards the entire device. An almost classic prefilled injection device is FlexPen® from Novo Nordisk A/S which is described in further details in WO 1999/38554. This injection device comprises a housing structure which includes a cartridge holder securing a cartridge containing 3 ml of a liquid drug.

When producing such prefilled injection devices, a large number of different tolerances apply. There are various tolerances in the moulding of the different parts making up the injection device. There are tolerances in the various click- and snap connections permanently connecting the individual parts, and there are tolerances in filling the liquid drug into the cartridge.

As a result of all these tolerances, the assembled injection device is usually delivered to the end user with an individual distance between the plunger inside the cartridge and the piston rod. This distance is referred to as air-gap. Before starting to use the injection device for injecting doses of the liquid drug, the user needs to remove this air-gap which is usually done by setting and ejecting small doses which henceforth moves the piston rod forward without actually ejecting any liquid drug. This process is often referred to as initial priming of the injection device. The first few empty (from liquid drug) dose ejections thus moves the piston rod into abutment with the plunger and only when contact has been established between the plunger and the piston rod will liquid drug be ejected, and the set dose sizes be correctly ejected.

In order to avoid the process of initially priming the injection device a large variety of different solutions has been proposed.

In WO 2009/095332 it has been suggested to provide a piston rod foot which can be slided axially relatively to the piston rod during assembly of the injection device and connected physically to the piston rod in a position wherein contact between the piston rod foot and the plunger has been established in the assembly process.

The point wherein the piston rod engages the plunger is often referred to as the zero point i.e. the point wherein the air-gap is zero, and the process of obtaining this position is henceforth referred to as a zero-point adjustment.

EP 2,968,777 describes a method wherein an adjusting member which is threaded to the piston rod is being rotated relatively to the housing structure during the assembly of the injection such that the piston rod is moved forward into contact with the plunger. Once contact has been established between the piston rod and the plunger this adjusting member is physically secured to the housing structure. When thereafter injections are taken, the adjusting member operates as a traditional nut element for helically advancing the rotatable piston rod.

A similar method wherein the nut element together with the piston rod is moved translational into the correct position and physically secured to the housing structure in that position is disclosed in WO 2017/001694.

Common for all the above solutions is that a physical connection such as e.g. welding is required during the assembly of the injection device. This obviously complicates the assembly of the injection device.

Recently a new type of pre-filled injection devices has been developed. These new injection devices are constructed to expel a limited and predefined number of dose volumes which dose volumes are both predetermined by the manufacturer of the injection device and equal in volume. This new type of injection devices are referred to as "Multi-use Fixed dose injection devices". When using such fixed dose injection device it is not possible for the user to set and eject small doses as all the dose volumes are predetermined by the producer of the fixed dose device. An example of such multi use fixed dose device is provided in WO 2018/007259. Such injection devices are very suitable for injecting liquid GLP-1 drugs which are usually injected in fixed dose volumes and typically administered once daily or once weekly.

Injection devices used for injecting insulin are usually provided with a so-called End-of-Content mechanism which ensures that a user cannot set a dose higher than the injectable content remaining in the injection device. When operating with insulin injection devices, the settable increments are typically very small and the injectable content in the cartridge has to be very precise. The standard content for insulin devices seems to be 3.0 ml. This typically requires that the free length the piston rod must be able to travel in order to expel the full injectable content of the cartridge before the End-of-Content mechanism reaches its locked position has to be very precise. For such insulin injection devices, it is henceforth not an option to use part of the free length of the piston rod for the zero-point adjustment since the free length the piston rod can move during ejection would then be too short to expel the entire injectable content leading to an incorrect operation of the End-of-Content mechanism. However, for multi-use fixed dose devices expelling larger doses, the exact free length of the piston rod is not that important. For such devices, it is sufficient if the free length is sufficiently long to expel the predefined number of dose volumes and at the same time securing that a further dose volume cannot be ejected. Consequently, for such injection devices it is acceptable to use a part of the free length of the piston rod for the zero-point adjustment.

DESCRIPTION OF THE INVENTION

It is an object of the present invention to provide a prefilled injection device wherein the air-gap can be more easily eliminated during the assembly of the injection device. It is preferably an object to eliminate the air gap without the use of a physical connection such as welding or the like.

Accordingly, in a first aspect of the invention a pre-filled injection device for delivering a liquid drug preferably in doses is provided. The pre-filled injection device comprises:

A housing structure which contains a volume of liquid drug. The liquid drug is contained in a cartridge which is permanently and non-removable secured in the housing structure. The liquid drug is expelled from the cartridge by having a movable plunger to be moved distally inside the cartridge, A piston rod which advances the movable plunger during dispensing. The piston rod is provided with an outer thread and a longitudinal track structure, A rotatable drive element engaging the longitudinal track structure of the piston rod, such that rotation of the drive element is transferred to a rotation of the piston rod, A nut element provided with a first thread engaging the outer thread of the piston rod, such that the piston rod is moved helically when rotated relatively to the nut element.

The piston rod is only allowed rotation in a first rotational direction relatively to the housing structure, the allowed rotational direction being the one that helically advances the piston rod in the dispensing direction.

Further, the nut element is rotatably coupled to the housing structure in a coupling provided with a one-way ratchet interface only allowing the nut element to be rotated in a second rotational direction opposite the first rotational direction.

The piston rod can henceforth only rotate in the dispensing direction (first rotational direction) and hence not be rotated in the second rotational direction moving the piston rod proximally in the injection device.

The nut element is rotatably mounted in the housing structure but is further provided with a one-way ratchet interface such that the nut element can only rotate in the second rotational direction opposite the first rotational direction.

The result being that when the nut element is rotated relatively to the housing structure in the allowed rotational direction (the second), the piston rod is moved in the distal direction without rotation. The rotation of the nut element cannot be transformed to a rotation of the piston rod as the allowed rotational direction of the nut element (second) lies against the allowed rotational direction of the piston rod (first).

The rotation of the nut element in the allowed rotational direction (second) thus translates the piston rod forward. The translation of the piston rod can be continued until the piston rod, or the piston rod foot if such is present, encounters and abuts the plunger inside the cartridge. Thereafter, the nut element cannot be rotated further. The wording "encounters and abut" is also to be understood in a virtual and calculated interpretation.

When expelling a liquid drug, the drive element is rotated which in turn rotates the piston rod in the allowed rotational direction (first). In this rotational direction, the nut element is prevented from rotation due to the ratchet engagement with the housing structure and the result is that the piston rod is rotated helically in the distal direction.

The prevention of rotation of the piston rod in one direction and the one-way interface between the nut element and the housing structure thus secures that the nut element can be rotated in the allowed direction (second) to minimize and preferably to eliminate any air-gap and at the same time assures that once contact between the piston rod (or foot) and the plunger is obtained, the nut is self-locking such that is cannot rotate in either direction.

In one rotational (first) direction the nut element is prevented from rotation by the one-way ratchet interface and in the opposite (second) direction the nut element is prevented from rotation due to the engagement between the piston rod (or foot) and the plunger. Consequently, there is no need to physically securing the nut element to the housing structure.

The longitudinal track structure of the piston rod is not necessarily a physical track as such but can be any geometrical form of the piston rod which the rotatable drive element is able to engage to transfer rotation, in one example the track structure can be a flange provided on the piston rod or alternatively it can be a flat longitudinal surface such that the piston rod has a not-circular cross section as e.g. disclosed in WO2017/001694.

The above principle can be used for any kind of pre-filled injection device wherein a threaded piston rod is advanced inside a cartridge by rotating the piston rod in relation to a threaded nut element carried or otherwise associated with a housing structure.

It is especially noted that all though many of the examples used throughout this application and especially in the more detailed part of the description relates to a so-called pre-filled multi-use fixed dose injection device, the general teaching of the application is suitable for a broad range of different pre-filled injection devices and are in no way limited to the specific examples. More specifically, the invention claimed in the annexed claims are in no way limited to the examples used.

In the broad range of Pre-filled injection devices covered by the annexed claims are also pre-filled injection devices having a dose setting mechanism by which a user can set a variety of individual dose sizes to be expelled in each expelling action.

The one-way ratchet interface established in the coupling zone between the nut element and the housing structure preferably comprises one or more flexible ratchet arms engaging a toothed surface. Either, the nut member or the housing structure can carry the flexible ratchet arms whereas the respective opposite element being the housing structure or the nut member carries the toothed surface. It is not important which constructional element carries the ratchet arms and which constructional element carries the toothed surface. The importance is the presence of a one-way coupling operational between the nut member and the housing structure.

The ratchet arms preferably extend in a radial direction perpendicular to the longitudinal extension of the injection device i.e. perpendicular to the centre axis "X". The interface between the ratchet arms and the toothed surface is designed such that only rotation in one rotational direction is allowed.

In one example wherein the piston rod is maintained in-rotatable and the nut element is rotated in the second rotational direction the piston rod translates in the dispensing direction.

Preventing the piston rod from rotation in the second rotational direction is preferably done by making the rotatable drive element engaging the piston rod rotatable only in the first rotational direction.

This is in one example done by providing a one-way ratchet between the drive element and the housing structure. This ratchet interface is designed such that the drive element can only rotate in the first rotational direction such that both the drive element and the piston rod is prevented form rotation in the second direction.

The one-way ratchet interface between the nut element and the housing structure thus allows the nut element to rotate in relation to the housing structure in a rotational direction which advances the piston rod in the dispensing direction. The rotation of the nut element is thus only possible as long as the air-gap is present. Once the piston rod (or the piston rod foot) encounters and abut the plunger inside the cartridge, the nut member is unable to rotate in the rotational direction moving the piston rod in the distal direction.

The housing structure of the injection device comprises a number of different parts which are preferably click fitted, glued or welded together to form one closed unit which also holds the cartridge such that the cartridge can only be separated from the housing structure by breaking the housing structure. Further, the housing structure comprises at least a housing part internally supporting a bridge structure such that the bridge structure is carried on an inner surface of the housing structure by a plurality of radial bearings.

The bridge structure is preferably a tube-like construction which is secured to the inner surface of the housing part by a number of radial bearings. Preferably, the bridge structure including the radial bearings are moulded as an integral part of the housing part. The longitudinal open areas provided between these radial bearings are usable to transform axial movement inside the housing structure.

In one example a connector element transforming axial movement from a needle shield to a drive element is provided and operational in these longitudinal openings.

In a further example is the toothed surface of the ratchet interface provided on the inside surface of a circular opening in the bridge structure.

In yet a further example, is the nut element provided with a thread on an outer surface which preferably engages a thread provided internally in the housing part and preferably in the circular opening in the bridge structure.

In one example the thread interface between the nut element and the housing structure comprises one or more protrusions on the one element and one or more helical flanges on the opposite element. The purpose of the thread interface is to displace the nut element in the proximal direction as a consequence of the nut element being rotated relatively to the housing structure.

If the pitch of the first threaded connection between the piston rod and the nut member is high i.e. the piston rod moves a long distance for each rotation, it is prudent to have a second threaded connection between the thread protrusions on the nut member and the thread flanges inside the housing part such that the nut member can be screwed helically in the proximal direction relatively to the housing structure during rotation of the nut member 11.

This has the benefit that when the nut member is rotated in the allowed direction, the nut member is moving proximally while it is moving the piston rod in the distal direction. Therefore, the pitch of the second threaded connection between the nut member and the housing structure must be subtracted from the pitch of the first threaded connection between the piston rod and the nut member in order to find the effective zero-point adjustment pitch.

A low effective pitch in the zero-point adjustment makes it easier to finetune the air-gap elimination process. It is thus beneficial to have a second threaded connection between the nut member and the housing part when operating with a piston rod with a high pitch which is the case when a relatively large volume has to be ejected for each rotation of the piston rod.

When the pitch of the first threaded connection between the piston rod and the nut member is low, a second threaded connection is not considered necessary and the nut member thus just needs to be rotational relatively to the housing structure without the ability to move axially.

The present invention further relates to a method for assembling such pre-filled injection device. The pre-filled injection device preferably being as defined herein, and having;

a nut element which is coupled to a housing structure of an injection device, a cartridge comprising a plunger is secured in the housing structure, the piston rod being able to be advanced in a expelling direction upon rotation of the piston rod relatively to the nut element in a first rotational direction, the nut element is rotationally coupled to the housing structure by a one-way ratchet interface, The method comprises the steps of:

i) securing the piston rod against rotation in a second rotational direction opposite to the first rotational direction, ii) rotating the nut element relatively to the housing structure in the second rotational direction advancing the piston rod in a direction towards the plunger.

By using this method when assembling the pre-filled injection device, the distance between the piston rod (or piston rod foot) and the plunger in the cartridge can easily be eliminated or at least significantly reduced during assembly of the injection device.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these or other geometries.

The term "Needle Cannula" is used to describe the actual conduit performing the penetration of the skin during injection. A needle cannula is usually made from a metallic material such as e.g. stainless steel and preferably connected to a hub made from a suitable material e.g. a polymer. A needle cannula could however also be made from a polymeric material or a glass material. The needle cannula e.g. mounted in the hub can either be exchangeable or permanently attached to the injection device.

As used herein, the term "Liquid drug" is meant to encompass any drug-containing flowable medicine capable of being passed through a delivery means such as a hollow needle cannula in a controlled manner, such as a liquid, solution, gel or fine suspension. Representative drugs could include pharmaceuticals such as peptides, proteins (e.g.

insulin, insulin analogues and C-peptide), and hormones, biologically derived or active agents, hormonal and gene based agents, nutritional formulas and other substances in both solid (dispensed) or liquid form.

"Cartridge" is the term used to describe the primary container actually containing the liquid drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end of the cartridge is typically closed by a plunger or piston made from a rubber composition or a suitable polymer. The plunger or piston can be slidable moved inside the cartridge. The space between the pierceable membrane and the movable plunger holds the liquid drug which is pressed out as the plunger decreased the volume of the space holding the liquid drug.

Since a cartridge usually has a narrow distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content. The injectable content in the cartridge must be at least equal to the volume making up the plurality of the predetermined sized dose volumes to be expelled. If in one example the multi-use fixed dose injection device is supposed to contain three fixed doses each having a volume of e.g. 0.3 ml, the injectable content of the cartridge needs to be at least 0.9 ml and the full volume of the cartridge must be larger to also include the volume that can not be expelled due to the narrow neck part.

By the term "Pre-filled" injection device is meant an injection device in which the cartridge containing the liquid drug is permanently embedded in the injection device such that it cannot be removed without permanent destruction of the injection device. Once the predetermined amount of liquid drug in the cartridge is used, the user normally discards the entire injection device. Usually the cartridge which has been filled by the manufacturer with a specific amount of liquid drug is secured in a cartridge holder which is then permanently connected in a housing structure such that the cartridge cannot be exchanged.

This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

A "Multi-Use Fixed Dose" injection device is meant to define an injection device which is able to deliver a predefined plurality (i.e. more than one) of doses which are substantially identical in volume. The liquid drug contained in the cartridge is thus expelled in a number of substantially identical dose volumes. In one example the cartridge could e.g. contain 3 ml of liquid drug which could e.g. be expelled in 6 identical doses each of 0.5 ml. The number of equally sized doses are often 2 to 8, and preferably 4 to 6 identical dose volumes. A multi-use fixed dose injection device can either be pre-filled such that the entire injection device is discarded after the predefined number of dose volumes has been expelled or it can be a durable injection device enabling the user to change the cartridge and expel a new series of equally sized doses volumes from the new cartridge.

Using the term "Automatic" in conjunction with injection device means that, the injection device is able to perform the injection without the user of the injection device delivering the force needed to expel the liquid drug during dosing. The force is typically delivered—automatically—by an electric motor or by a spring drive. The actual spring for the spring drive is e.g. strained by the user during dose setting, however, such springs are usually pre-strained with a low force in order to avoid problems of delivering very small doses. Alternatively, the spring can be fully preloaded by the manufacturer with a preloaded force sufficient to expel the full initial content (i.e. the entire injectable content) of liquid drug contained in the cartridge though a number of doses. Typically, the user activates a release mechanism provided either on the surface of the housing or at the proximal end of the injection device to partially release some of the force accumulated in the spring when carrying out the injection. Alternatively, the injection device can be shield triggered such that the activation of a movable shield releases the force required to expel the dose.

The term "Permanently connected" or "permanently embedded" as used in this description is intended to mean that the parts, and especially the cartridge permanently embedded in the housing structure, requires the use of tools in order to be separated and should the parts be separated it would permanently damage at least one of the parts thus rendering the injection device unable to operate.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clock-wise" and "counter clock-wise" or similar relative expressions are used, these only refer to the appended figures and not to an actual situation of use. The shown figures are schematic representations for which reason the configuration of the different structures as well as their relative dimensions are intended to serve illustrative purposes only.

Figure 2A:
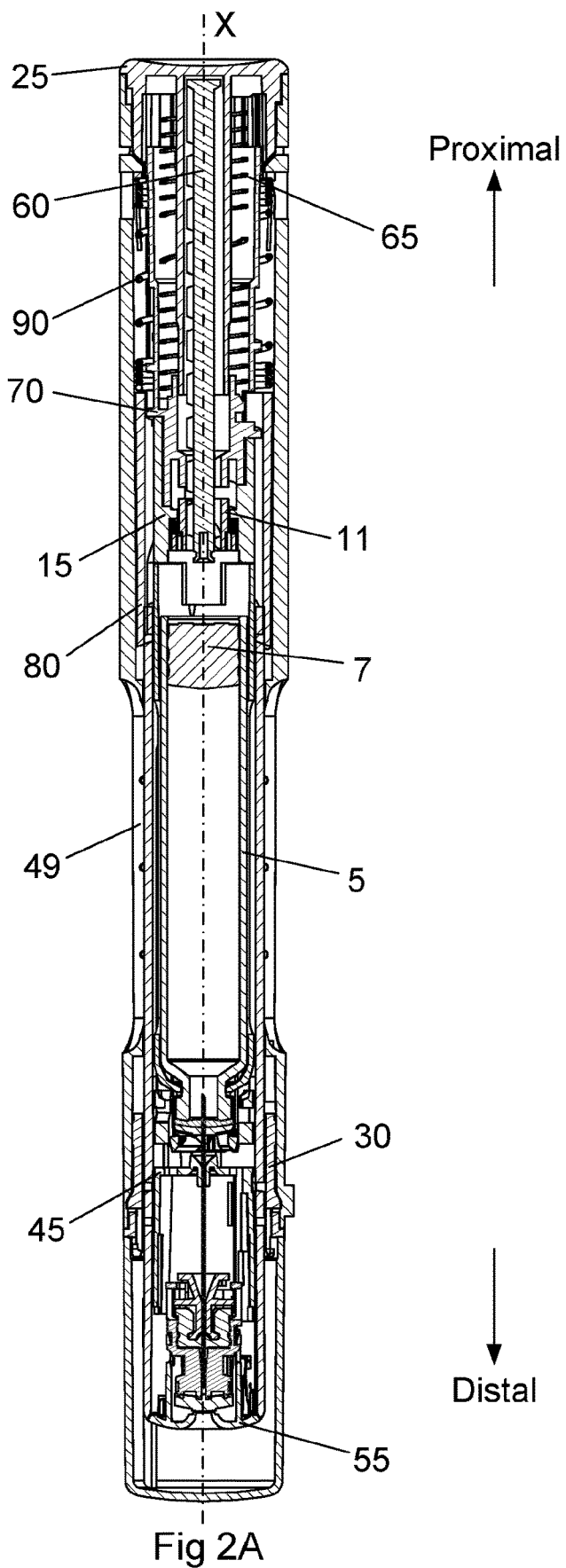
FIG. 2A-B shows a cross-sectional view of the spring driven injection device of FIG. 1. The view in FIG. 2B is rotated 90° relatively to FIG. 2A.
Figure 2B:
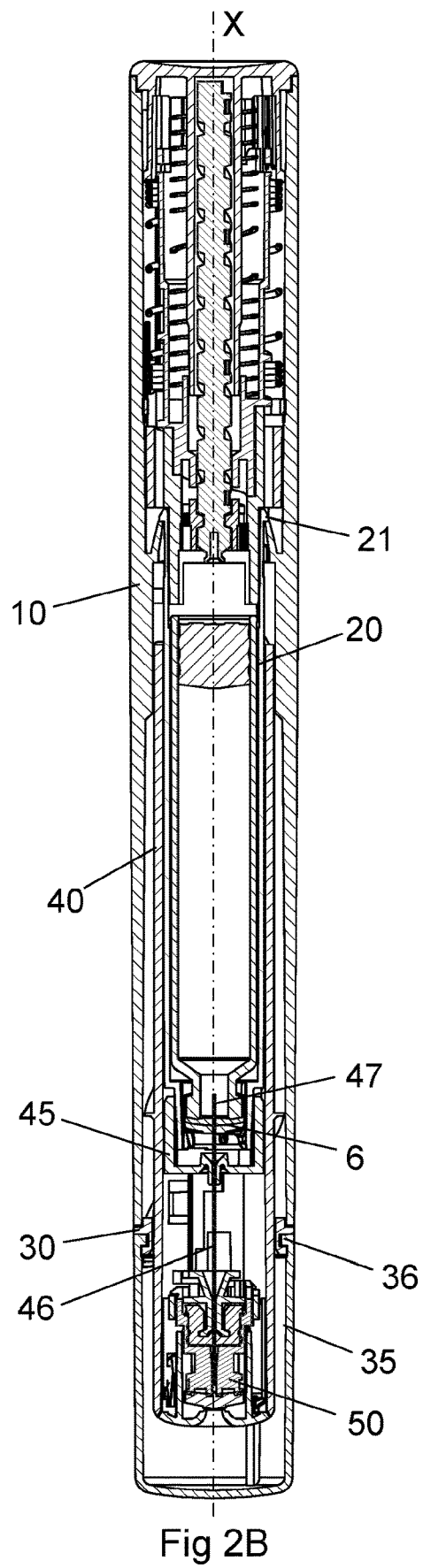

In that context it may be convenient to define that the term "distal end" in the appended figures is meant to refer to the end of the injection device securing the needle cannula and pointing towards the user during injection, whereas the term "proximal end" is meant to refer to be the opposite end as indicated in FIG. 2A-B. Distal and proximal are meant to be along an axial orientation extending along the longitudinal axis (X) of the injection device as also disclosed in FIG. 2A-2B.

When referring to clock-wise and anti or counter clock-wise in the following examples it is understood that the injection device is viewed from a position distal to the injection device. Clock-wise is thus a rotation towards the right side like the arms on a clock and counter clock-wise is a rotation towards the left side.

To explain the various movements taken place in the injection device described, the following terminology are used throughout the following detailed description;

"Translational movement" is meant to be a strictly linear movement without any rotation.

"Rotational movement" is any movement of rotation around a centre which centre can be a centre point i.e. in one planar or a centre axis i.e. having a longitudinal extension.

"Axial movement" means any movement in an axial direction. Such movement can be a strictly translational movement or include a rotational movement which thus makes it a "Helically movement" as this is meant to be the combination of an axial movement and a rotational movement.

"Telescopic" is meant to cover the situation in which a movable element moves out from, and/or into, a base element. The telescopic movement can be either translational or include a rotation thus making the movement helical.

Figure 1:
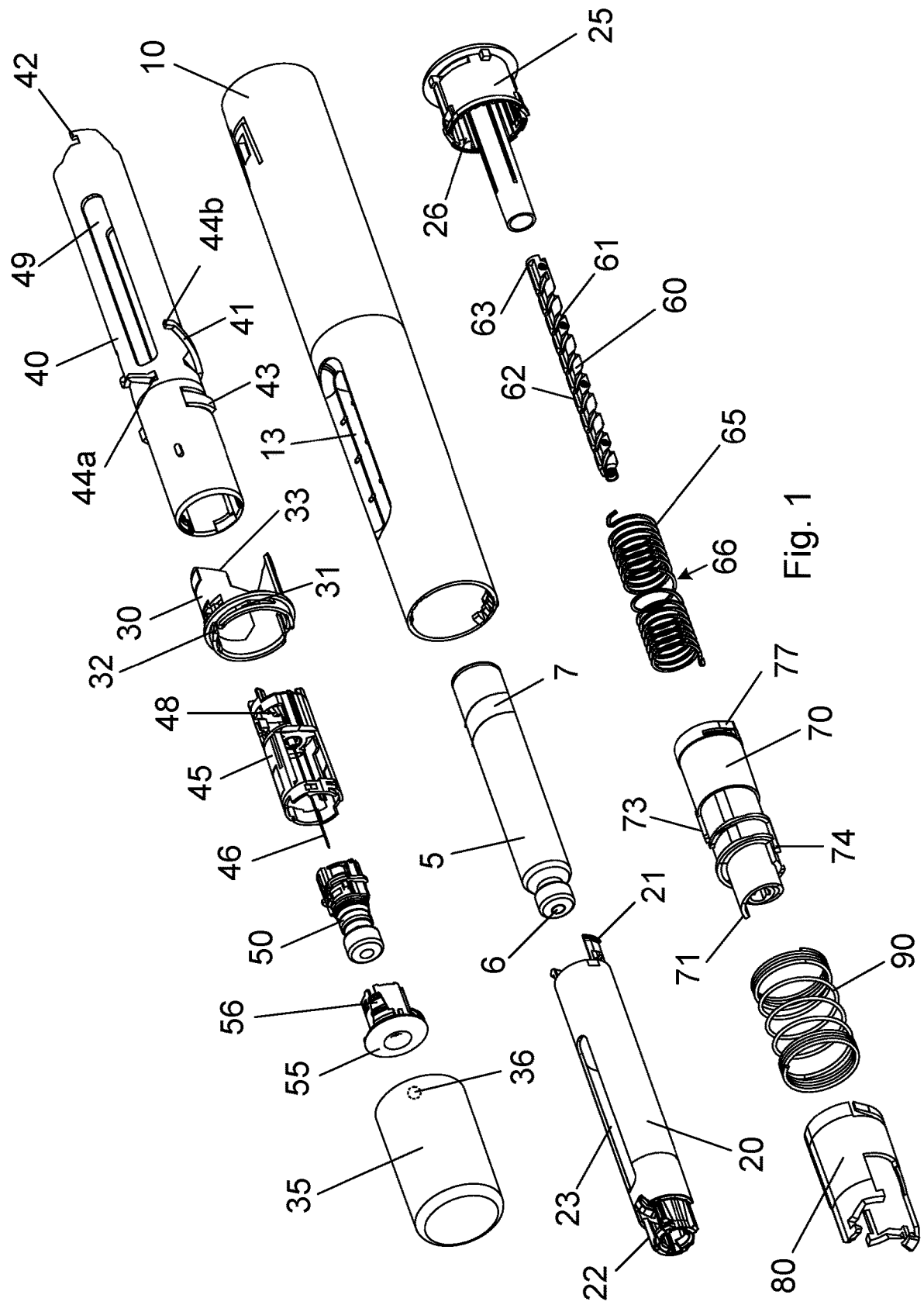
FIG. 1 shows an exploded view of the spring driven injection device according to one example of the invention.

FIG. 1 disclose an exploded view of a spring injection device according to an example of the invention. In the disclosed example the injection device is pen-shaped which is also often referred to as an injection pen.

Figure 13:
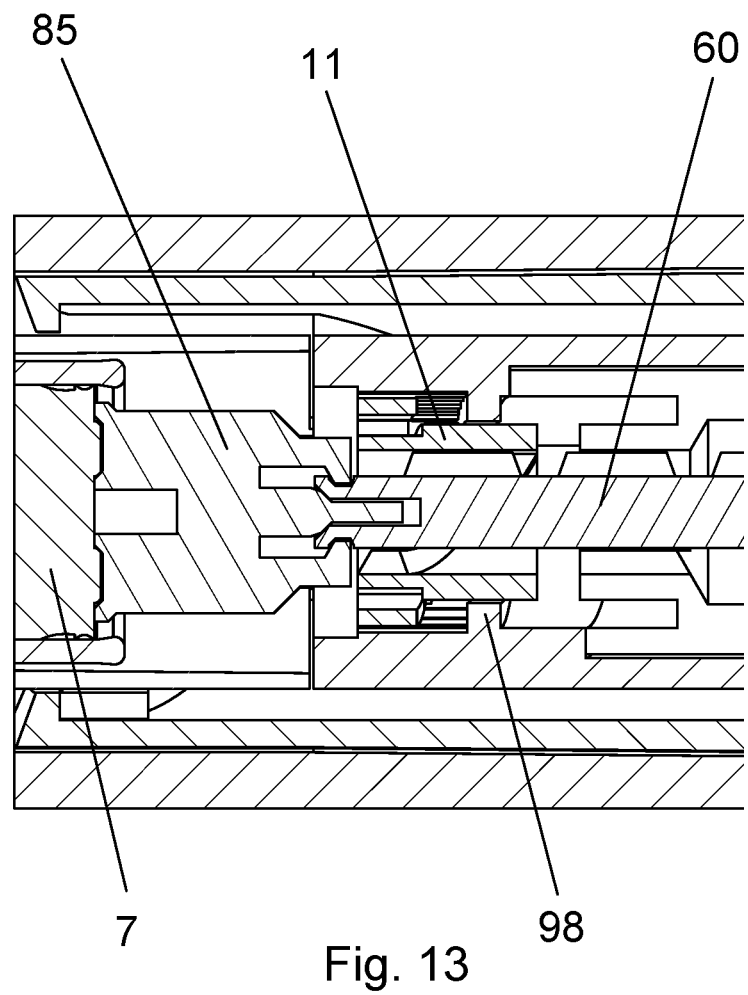
FIG. 13 shows a view of the zero-point adjustment in the first example.

The liquid drug to be ejected is contained in a cartridge 5 which is generally a hollow glass ampoule which is sealed at the distal end by a pierceable septum 6 and at the proximal end by a movable plunger 7. The moveable plunger 7 is arranged to be moved in the distal direction by a piston rod 60. In order to properly distribute the force from the piston rod 60 and on to the plunger 7, a piston rod foot 85 can be provided between the piston rod 60 and the plunger 7 as depicted in FIG. 13.

The cartridge 5 is typically filled with the liquid drug by the manufacturer and permanently and non-exchangeable secured in a housing structure of the injection device, thus making the injection device a pre-filled injection device. The housing structure as disclosed comprises a housing part 10, a cartridge holder 20, a spring base 25 and a shield guide 30. The housing structure can however comprise any number of components or alternatively be moulded as one single housing unit.

Figure 15:
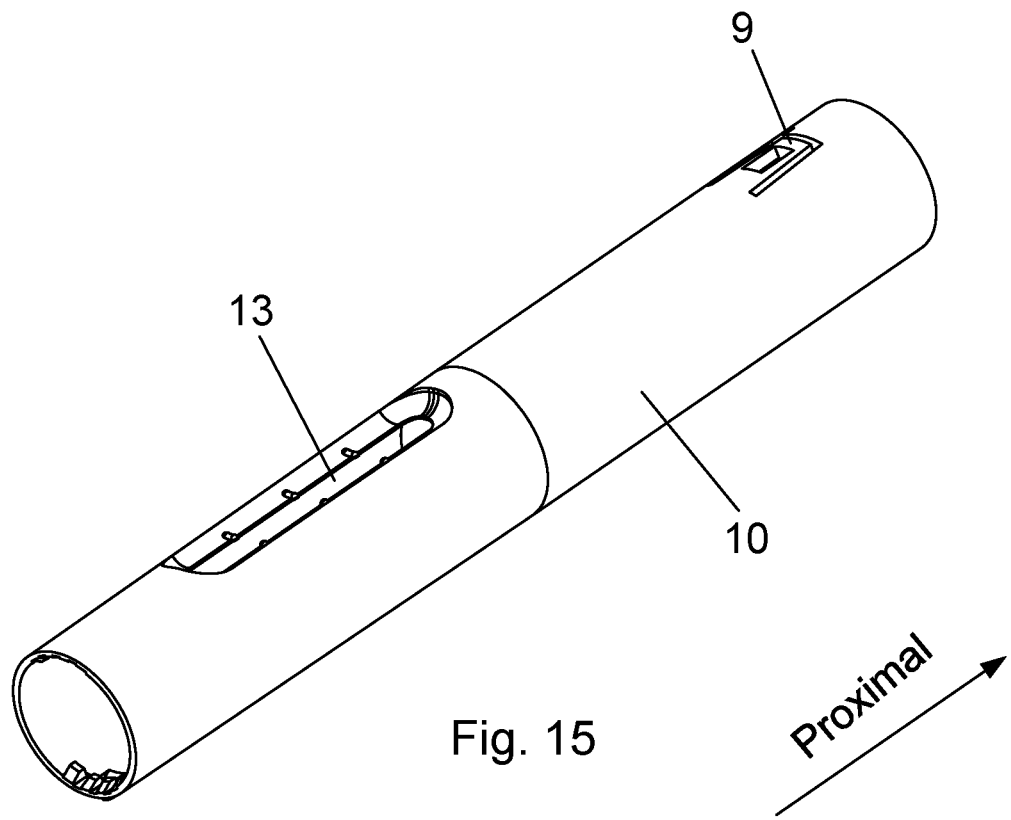
FIG. 15 shows a perspective view of the housing part.

The housing part 10 (also shown in FIG. 15), the cartridge holder 20, the spring base 25 and the shield guide 30 are preferably permanently secured to each other such that the cartridge 5 is permanently encapsulated in the housing structure thus making up a pre-filled injection device. Proximally, the housing part 10 is closed by the spring base 25 which is click fitted to the housing part 10 during assembly of the prefilled injection device. Distally on the housing part 10, the shield guide 30 is also click fitted to the housing part 10. The cartridge holder 20 is preferably permanently secured to the housing part 10 by a pair of resilient click arms 21 or alternatively by being moulded integral with the housing part 10.

All though the figures depict one pair of resilient click arms 21 any number of arms can be provided. Since the example herein refer to a pen-shaped injection device having a tubular cross-section many of the variety of protrusion, arms, guiding tracks and other mechanical elements are provided in pairs of two. However, for many of these attributes any random number can be provided.

The shield guide 30 guides a telescopically movable shield 40, the function of which will be explained later. Distally the shield guide 30 is on the outer surface provided with a peripheral track 31 with an axial opening 32. This peripheral track 31 guides a radially pointing protrusion 36 located on the inner surface of the protective cap 35 as disclosed in FIG. 2B (and indicated with broken lines in FIG. 1). The user is henceforth required to rotate the protective cap 35 in the counter clock-wise direction (when viewed from a distal position) relatively to the shield guide 30 and thus to the housing structure before the radially pointing protrusion 36 can be moved axially out through the axial opening 32 and the protective cap 35 can be removed.

Distally the cartridge holder 20 is, at least in use, provided with a needle hub 45 carrying a needle cannula 46. Alternatively, a needle magazine with a plurality of needle cannulae can be integrated into the injection device.

As disclosed e.g. in FIGS. 2A and 2B, the needle cannula 46 has a distal tip for penetrating the skin of a user during injection and a proximal end 47 which is penetrated through the septum 6 of the cartridge 5 such that the liquid drug can be pressed out from the cartridge 5 and flow through the lumen of the needle cannula 46 and through the skin of the user.

The needle hub 45 is secured to the cartridge holder 20 by an interface which is activated in an initiation process. During this initiation process the needle hub 45 is moved axially in the proximal direction such that a proximal end 47 of the needle cannula 46 penetrates through the septum 6 of the cartridge 5. Also, in the sequence of moving the needle hub 45, proximalty locking arms 48 provided on the needle hub 45 irreversible engage and locks to the distal interface 22 on the cartridge holder 20 such that the needle hub 45 hereafter is irreversible locked to the cartridge holder 20.

The needle hub 45 is preferably moved in the proximal direction by a rotation of the telescopically movable shield 40 which through a helical interface is able to move the needle hub 45 proximally. Once the initiation process has been completed, the locking arm 48 on the needle hub 45 locks to the cartridge holder 20 and click arms 43 provided on the telescopically movable shield 40 engages the housing structure and prevents the user from rotating the telescopically movable shield 40 back into the previous position. The engagement of the click arms 43 are preferably with an axial inner surface of the shield guide 30 which is secured to the housing part 10. The initiation process can henceforth only be performed one time.

After the initiation process has been completed, the injection device is in the ready-to-use state as disclosed in FIG. 2A-B and the user can use the injection device for multiple injections as will be explained. As further explained, the injection of the liquid drug is driven by a spring which in the disclosed example is a torsion spring which delivers a torsional force. However, any kind of spring can be used for the injection process.

The telescopically movable shield 40 carries a cleaning assembly 50 which is disclosed in further details in WO 2019/101670. This cleaning assembly 50 keeps the distal end of the needle cannula 46 biological clean between injections and is secured to the telescopically movable shield 40 by the shield tip 55 which is click fitted to the telescopically movable shield 40 by resilient arms 56 engaging the telescopically movable shield 40, such that the cleaning assembly 50 follows all movements of the telescopically movable shield 40 i.e. both rotational, translational and helical movements.

The cleaning assembly 50 preferably contains a liquid cleaning agent which in one example can be the same preservative as contained in the liquid drug in the cartridge 5. In a preferred example, the cleaning agent is the identical same preservative containing pharmaceutical liquid drug as contained in the cartridge 5 which is filled into the cleaning assembly 50 during the initiation of the injection device.

A torsion spring arrangement is provided to move the piston rod 60 in the distal direction during dose expelling. The torsion spring arrangement comprises a torsion spring 65, a drive tube 70 and an internal nut member 11 for driving the piston rod 60 in the distal direction as will be explained.

The torsion spring 65 is in the disclosed example a metal spring wherein a wire is coiled helically. In the longitudinal direction, the torsion spring 65 can be divided into different zones or areas. In some of these zones the wire in the coil has no, or only very little, distance between the coils and in other zones the coils have a significant longitudinal distance between the coils. These zones are referred to as compression zones 66 (see e.g. FIG. 1). Such compression zones 66 with a distance between the coils provide a compression force such that the torsion spring 65 can apply both a torsional force and a compression force. When the two ends of the torsion spring 65 are compressed towards each other, the torsion spring 65 returns a force directed in the longitudinal direction and urging the two ends away from each other.

The two ends of the torsion spring 65 are bended into hooks. One hook is attached to the housing structure via the spring base 25 at a proximal end of the injection device and the other hook is attached to the drive tube 70 at an opposite and more distal end of the injection device. A torsional force can thus be provided between the housing structure and the drive tube 70 which torsional force can be used to rotate the drive tube 70.

The torsion spring 65 is preferably mounted by passing the hooks through axial openings in the respective parts 25, 70 followed by a relative rotation of the respective part 25, 70 and the torsion spring 65 such that the hook is captured by the edges of the axial openings. The torsion spring 65 is preferably first engaged with the drive tube 70 and later in the assembly process with the spring base 25. Both the drive tube and the spring base can in one example be provided with snap protrusions as will be explained.

Figure 3:
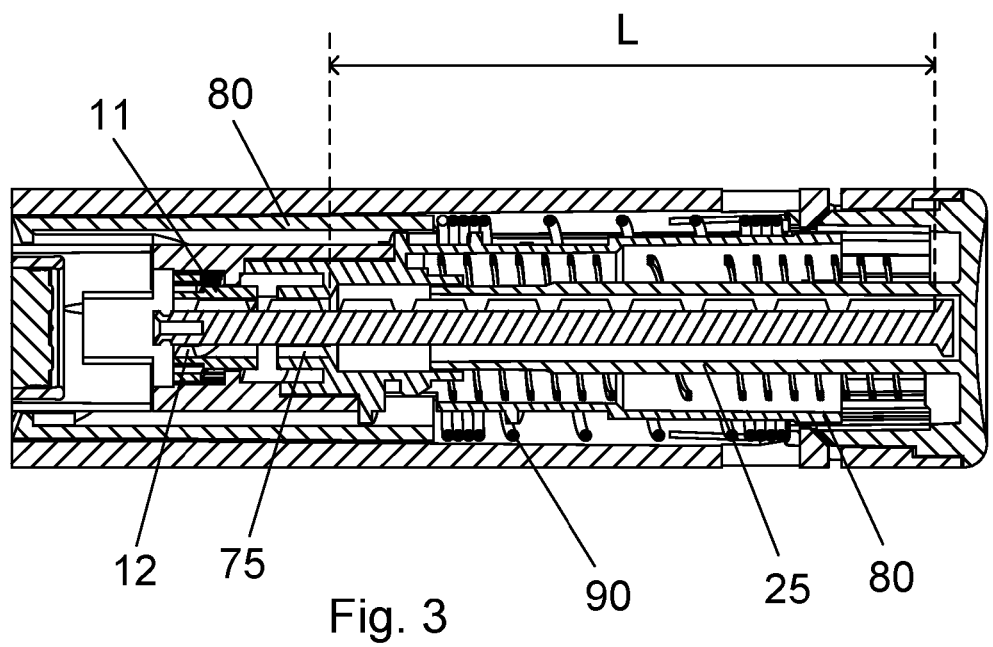
FIG. 3 shows a cross-sectional view of the proximal part of the spring driven injection device with the piston rod positioned in the initial position. The view in FIG. 3 is rotated 90° relatively to FIG. 4.
Figure 4:
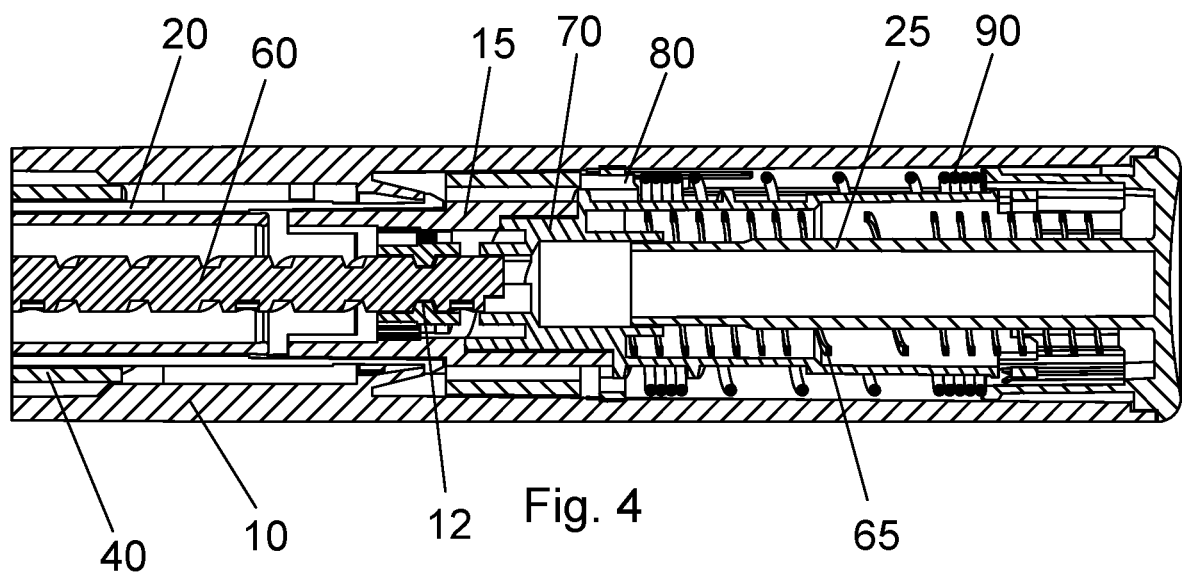
FIG. 4 shows a cross-sectional view of the proximal part of the spring driven injection device with the piston rod positioned in the stop position. The view in FIG. 4 is rotated 90° relatively to FIG. 3.
Figure 8:
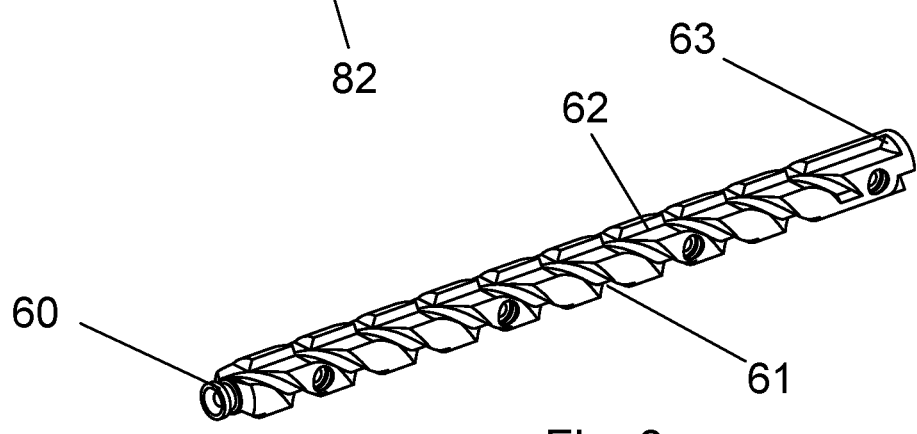
FIG. 8 shows a perspective view of the piston rod.

The piston rod 60 which is disclosed in detail in FIG. 8 is on the outer surface provided with an outer thread 61 and is further provided with a longitudinal track structure 62 which is open at the distal end but at the proximal end terminates in a stop surface 63. The longitudinal track structure 62 has a free length called "L". The free length "L" can best be seen in FIGS. 3 and 5A and is the length measured from the engagement of the inwardly pointing protrusion 75 on the drive tube 70 with the piston rod 60 and to the stop surface 63 at the proximal end of the track structure 62 as will be explained. The free length "L" is thus an expression for the axial length that the piston rod 60 is able to move in the distal direction before the stop surface 63 engage the inwardly pointing protrusion 75. Accordingly, the free length "L" is shorter than the actual length of the track structure 62 as also seen in FIG. 3.

The longitudinal track structure 62 refer to any kind of structure provided in or on the piston rod 60 which is able to define a longitudinal free length "L". It can e.g. be any kind of track, groove or similar indentation.

The internal nut member 11 is fixed to the housing structure both rotational and axially. In one example, the nut member 11 is an integral part of the housing part 10. Alternatively, the nut member 11 can be a separate part which is secured to the housing part 10 during assembly of the injection device e.g. by gluing or welding. The nut member 11 is on an inner surface provided with an inner thread 12 which engages with the outer thread 61 on the piston rod 60 such that the piston rod 60 is moved helically when it is rotated relatively to the housing structure.

As disclosed in FIGS. 12 to 17A-B it is in a further embodiment possible to utilize the nut member 11 for air-gap elimination during assembly of the injection device as will be explained.

The longitudinal track structure 62 on the piston rod 60 is engaged by an inwardly pointing protrusion 75 provided on an inner surface of the drive tube 70 such that whenever the drive tube 70 is rotated, the piston rod 60 rotates simultaneously and is thus moved helically in the distal direction in the inner thread 12 of the nut member 11. The inwardly pointing protrusion 75 disclosed in FIG. 6A-B is preferably provided in pairs but can be provided in singularity or in any random number.

The torsion spring 65 is encompassed between the housing structure and the drive tube 70 such that the torque stored in the torsion spring 65 can rotate the drive tube 70 relatively to the housing structure. In the disclosed embodiment, the torsion spring 65 engages the drive tube 70 at its distal end and the spring base 25 at its proximal end. The torsion spring 65 is strained during the manufacturing of the injection device i.e. during assembly of the injection device, such that a relatively high torque is stored in the torsion spring 65 when the injection device is delivered to the user. The torque stored in the unused delivery state of the injection device is preferably sufficient to expel the entire initial content of the cartridge 5 which means that the torque is sufficient to drive the piston rod 60 and thus the plunger 7 to, or near to, the distal end of the cartridge 5. In a preferred example such multiple-use fixed dose injection device would have a torsion spring 65 which is strained and ready to expel approximately 2 to 8 predetermined and equally sized dose volumes such that the user does not need to strain the torsion spring 65 between each of these 2 to 8 injections.

Figure 6A:
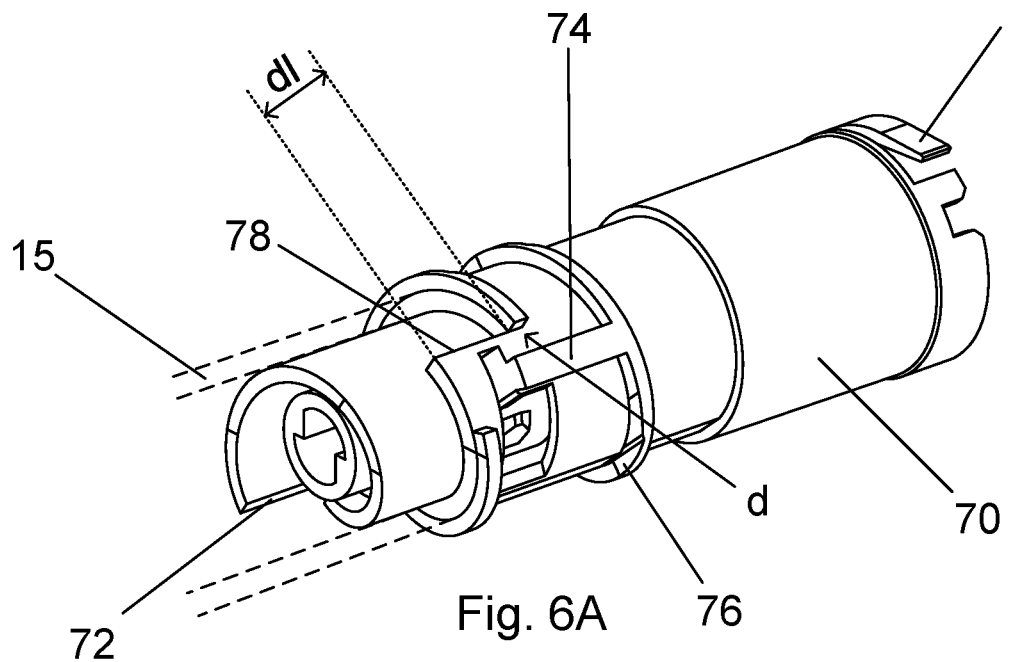
FIG. 6A-B shows perspective views of the drive tube viewed from different angles.
Figure 6B:
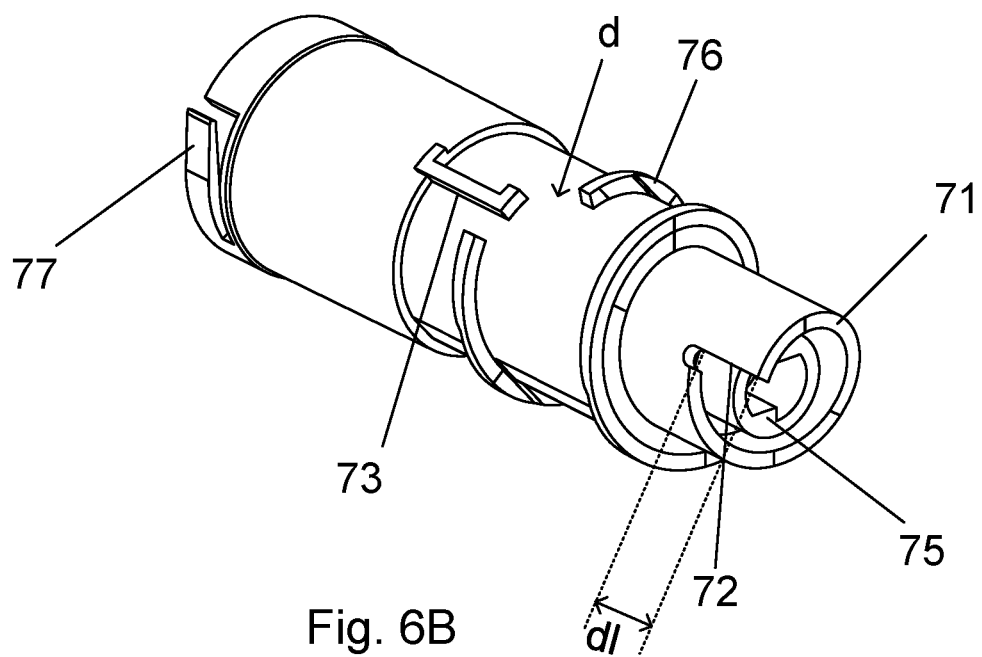

The drive tube 70 as disclosed in FIG. 6A-B has at its distal end a first helical shape 71 i.e. the distal end of the drive tube 70 is made from a sleeve which progressively falls away in a circumferential direction. The first helical shape 71 extend in the axial direction and terminates in a first axial drive flange 72.

Further, the most distal part of the drive tube 70 has an outer surface which is radially offset in relation to the remaining part of the drive tube 70. This radial indentation in the outer surface of the drive tube 70 defines a second axial drive flange 78 which is parallel to the first axial drive flange 72 but rotationally offset by 180° as best seen in FIG. 6A. These two axial flanges 72, 78 defines a stop for the rotation of the drive tube 70 as will be explained.

Figure 17A:
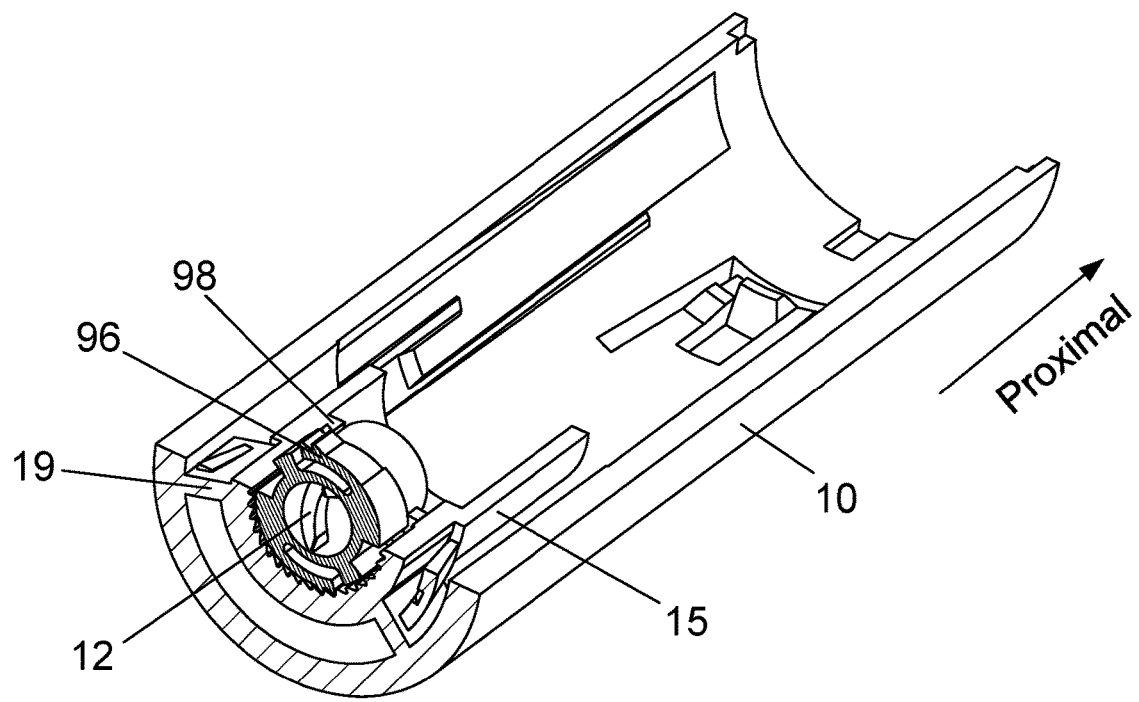
FIG. 17A-B shows two cut-open images of the interface between the nut member and the housing part for the zero-point adjustment.
Figure 17B:
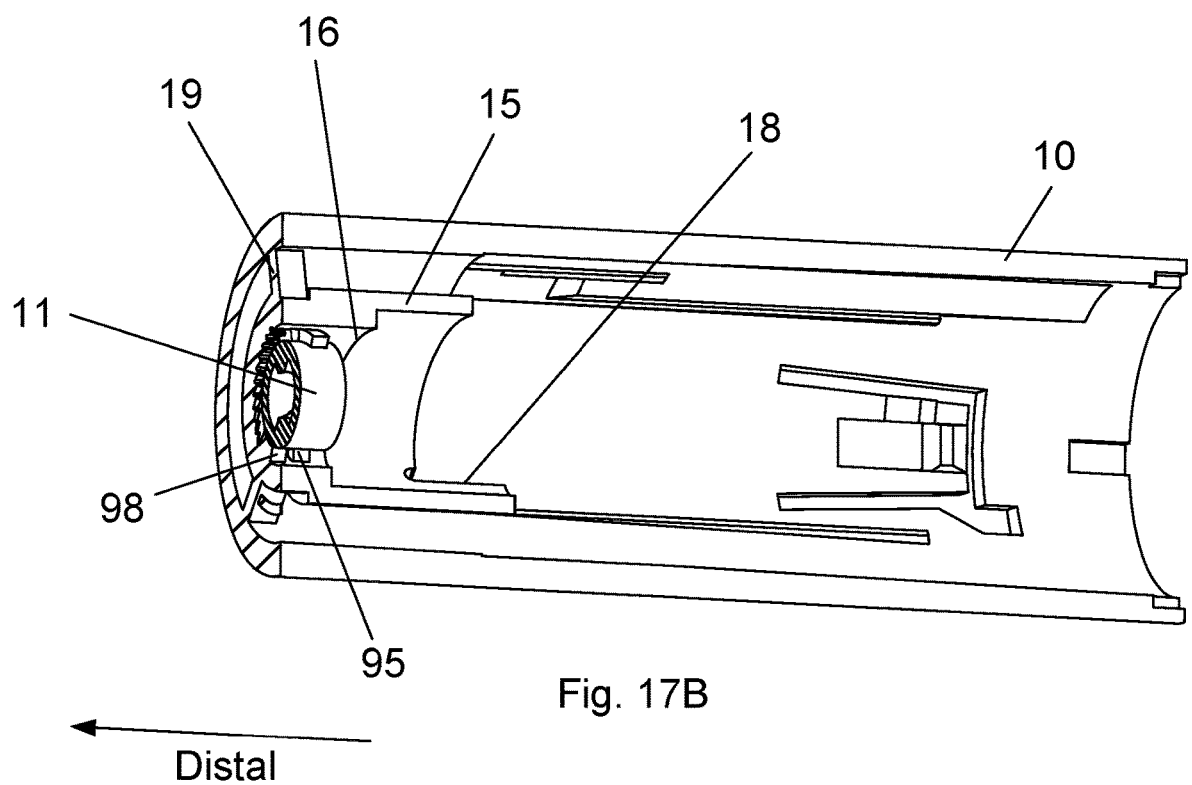

Leading up to the second axial drive flange 78 the radial indentation has a helical structure forming a helical surface to abut against a similar helical surface provided inside the housing structure. This helical surface has the same configuration as the housing helical shape 16 but is longitudinal offset in the proximal direction as best seen in FIG. 17B. The interface between these two surfaces has the same effect as the interface between the first helical shape 71 and the housing helical shape 16 as will be explained. Having two such helical interfaces makes the operation of the injection device more stable.

Further, two outwardly pointing protuberances 73, 74 are provided on the outer surface of the drive tube 70. These two protuberances 73, 74 are in the disclosed example also 180° offset in relation to each other and also offset a distance in the longitudinal direction.

As explained, one or more inwardly pointing protrusions 75 inside the drive tube 70 engages the longitudinal track structure 62 in the piston rod 60. On the outer surface, the drive tube 70 is provided with a helical flange 76, the use of which will be explained later.

The housing part 10 of the housing structure is internally moulded with an internal bridge structure 15 having an axial opening allowing the piston rod 60 to move through this opening. On the inside surface the bridge structure 15 guides and supports the distal part of the drive tube 70. This guiding is indicated in FIG. 6A wherein the contour of the bridge structure 15 is shown with broken lines. The bridge structure 15 which also carries the nut member 11 can in one example be moulded separately and attached to the housing part 10. In both cases the bridge part 15 is only in contact with the housing part 10 via radial bearing parts 19 which only obtain a limited angular space such that axial openings around the bridge part 15 are present. This is best seen in FIG. 17A-B.

The first helical shape 71 at the distal end of the drive tube 70 engages a similar helical shape 16 (see e.g. FIG. 10) which also extend in the axial direction and which is provided in the bridge structure 15 inside the housing part 10 of the housing structure (hereafter referred to as the housing helical shape 16). This housing helical shape 16 is, as the first helical shape 71, a sleeve that progressively falls away in a circumferential direction and terminates in a first axial housing flange 17 which is able to engage with the first axial drive flange 72 of the drive tube 70.

Figure 9:
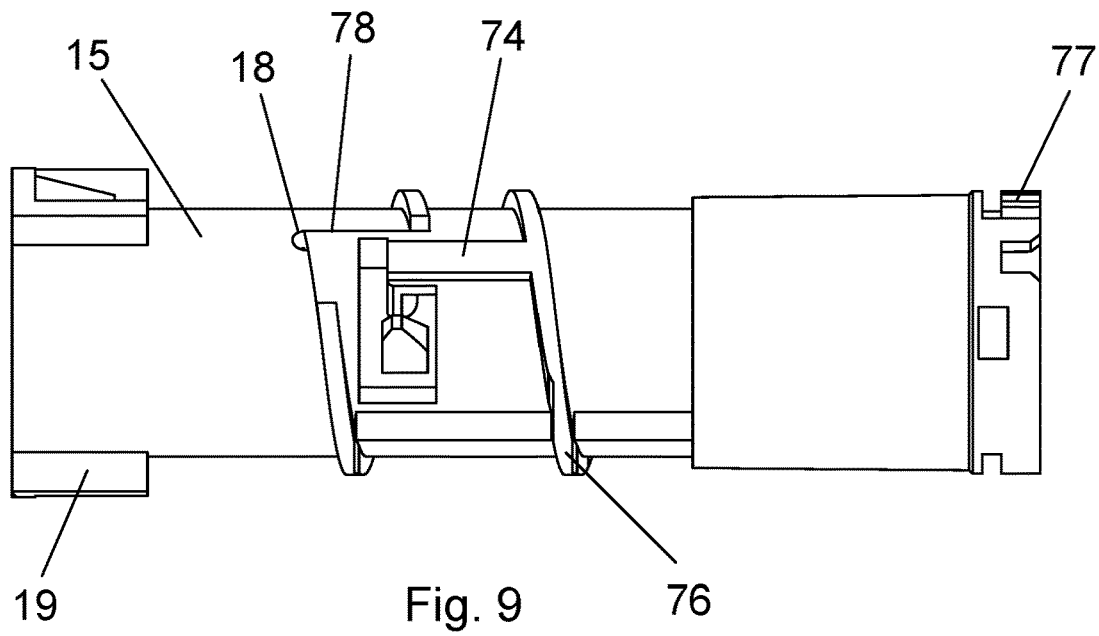
FIG. 9 shows a side-view of the interface between the drive tube and the bridge structure inside housing structure.
Figure 10:
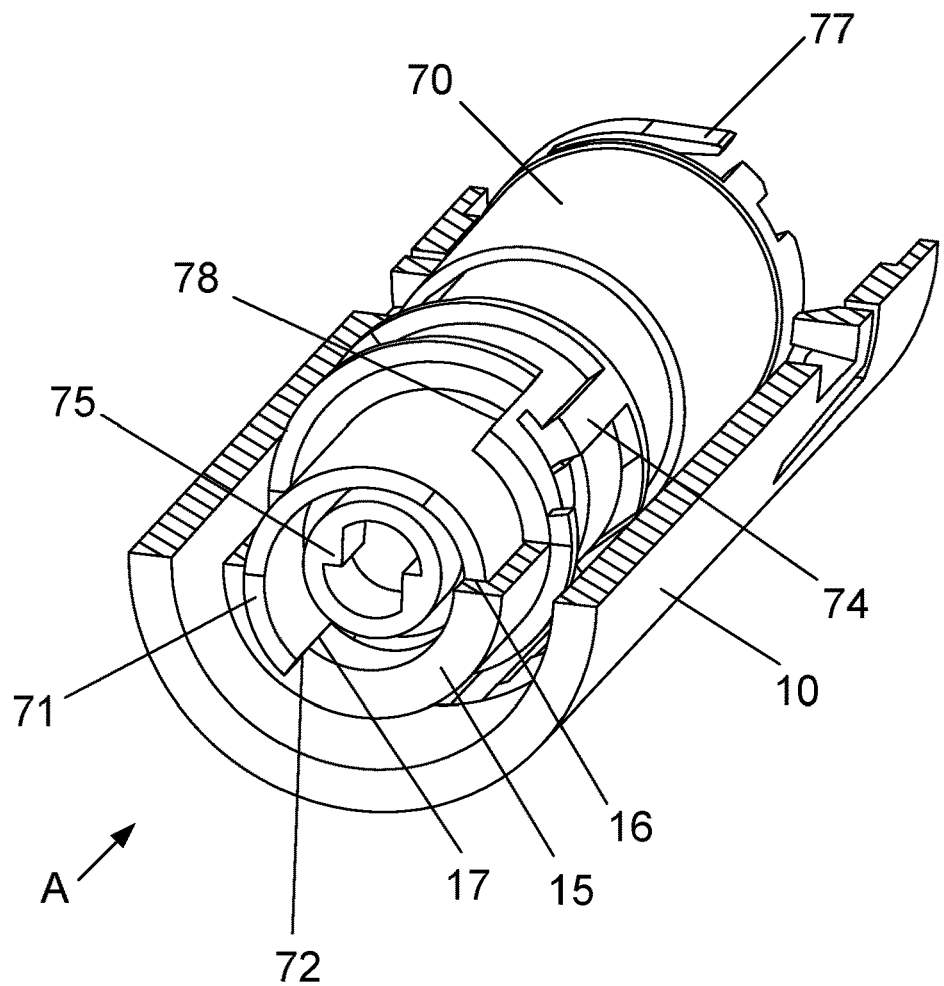
FIG. 10 shows a cut-open view of the interface between the drive tube and the housing structure.

FIG. 9 discloses the interface between the drive tube 70 and the bridge structure 15 located inside the housing part 10 i.e. the housing part 10 is visionally cut away. FIG. 10 discloses the interface between the drive tube 70 and the housing structure including the bridge structure 15. In the view in FIG. 10, the housing structure, but not the drive tube 70, is radially cut along the line "A" in FIG. 5A and viewed from a distal position. The cut thus runs through the first axial housing flange 17. The housing part 10 is further visually cut open in a longitudinal planar following the centre line "X".

The internal bridge structure 15 is further provided with a second axial housing flange 18 as seen in FIG. 9 and in FIG. 17B which is able to abut the second axial drive flange 78. The rotational engagement between the drive tube 70 and the housing structure are thus defined by the abutment of the first axial drive flange 72 and the first axial housing flange 17 together with the second axial drive flange 78 and the second axial housing flange 18 as best in FIGS. 9 and 10. All four flanges 72, 17; 78, 18 are preferably parallel both with each other and with the longitudinal centre axis "X" of the injection device. Further, the axial length ("dl", indicated on FIG. 6A-B) of these four flanges 72, 17; 78, 18 are the same as will be explained.

As the torsion spring 65 constantly apply a torsional force onto the drive tube 70, the drive tube 70 will rotate in the counter clock-wise direction (in the example) when seen from the distal end of the injection device. However, the engagement between the first axial drive flange 72 and the first axial housing flange 17 and between the second axial drive flange 78 and the second axial housing flange 18 prevents the drive tube 70 from rotation relatively to the housing structure.

Further, a number of ratchet arms 77 provided on the drive tube 70 engages a tooting 26 inside the spring base 25 such that the drive tube 70 is only rotational in one direction which in the disclosed example is the counter clock-wise direction when the injection device is viewed from a distal position. This is e.g. illustrated in FIG. 5B The telescopically movable shield 40 is rotatable in relation to the housing structure and can be rotated between a locked and an unlocked position. As seen in FIG. 1, the telescopically movable shield 40 is on its outer surface provided with a helical structure 41 which terminates in radial ends 44a,b which are positioned an angular distance apart such that these radial ends 44a,b together defines an axial opening. On an inner surface of the housing part 10 an inwardly pointing protrusion is provided which is able to slide through the axial opening of the helical structure 41 when the telescopically movable shield 40 has been rotated to the unlocked position. In any other position this inwardly pointing protrusion will abut the helical structure 41 if the telescopically movable shield 40 is attempted to be moved translational in the proximal direction which henceforth defines the locked position.

The helical structure 41 further forces the needle shield 40 to move helically when rotated. It is thus possible to move the needle shield 40 to a position wherein the distal tip of the needle cannula 46 is positioned just outside the cleaning assembly 50 when the needle shield 40 is unlocked.

In the locked position the telescopically movable shield 40 is prevented from moving translational whereas, in the unlocked position, the telescopically movable shield 40 is able to move translational. In this context translational is meant to define an axial movement along the centre axis "X" without any rotation.

The housing part 10 is provided with a pair of longitudinal windows 13. These longitudinal windows 13 are aligned with similar windows 23 provided in the cartridge holder 20 such that the user is able to visually inspect the content of the cartridge 5. The telescopically movable shield 40 which is radially sandwiched between the housing part 10 and the cartridge holder 20 is rotatable between a locked and an unlocked position and is provided with a further set of windows 49. These windows 49 are aligned with the other windows 13, 23 such that the user is only able to view the content of the cartridge 5 when the telescopically movable shield 40 has been rotated to its unlocked position. When the telescopically movable shield 40 is in the locked position, the solid part of the telescopically movable shield 40 hinders the user from visually seeing the cartridge 5. This rotation of the set of windows 49 in the telescopically movable shield 40 thus also indicates when the injection device is ready for injection.

In one example, the pair of longitudinal windows 13 provided in the housing part 10 can be provided with a scale showing the plurality of doses in the injection device. In the example in FIG. 1 and FIG. 15, this scale indicates four sections each representing one of the predetermined dose volumes. The user is thus able to visually see the physical position of the plunger 7 in the sections in the windows 13 and henceforth see how many doses has been taken and how many remains in the cartridge 5.

The telescopically movable shield 40 is also used to release the torque stored in the torsion spring 65 to thereby eject the predetermined dose volume when moved translational in the proximal direction. During injection, the user presses the shield tip 55 and henceforth the telescopically movable shield 40 against the skin whereby the telescopically movable shield 40 is moved in the proximal direction.

Figure 7A:
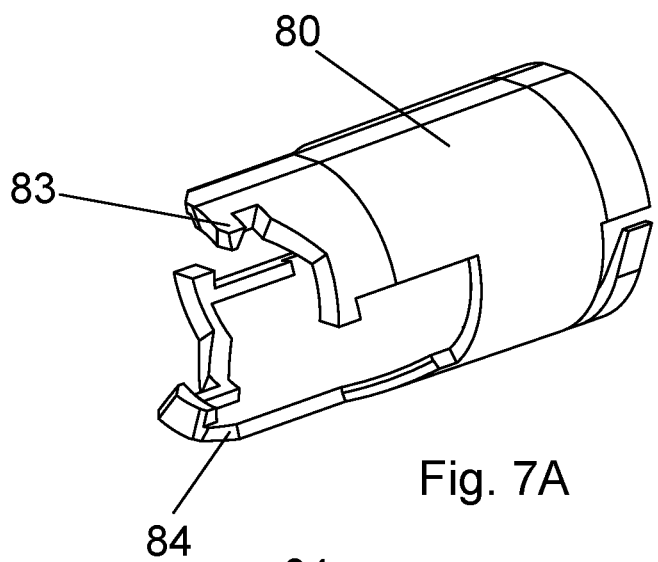
FIG. 7A-B shows perspective views of the connector viewed from opposite ends.
Figure 7B:
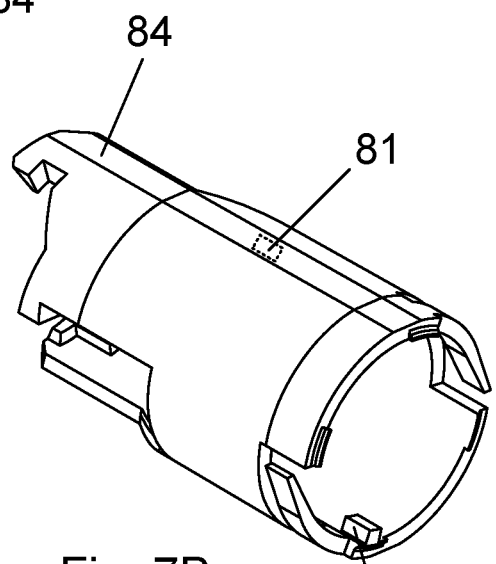

To transfer the translational movement from the telescopically movable shield 40 to the drive tube 70, a connector element 80 as disclosed in FIG. 7A-B is provided. This connector element 80 is guided translational i.e. without any rotation, in relation to the housing part 10 and is on its inner surface provided with two inwardly pointing protuberances 81, 82 which are also offset both rotational and axially.

One (indicated as "81") of the two inwardly pointing protuberances 81, 82 are not directly visible in the enclosed figures but is indicated with punctured lines in FIG. 7B. The two protuberances 81, 82 are in the disclosed example offset 180° relatively to each other.

Both the telescopically movable shield 40 and the connector element 80 are provided with hooks 42, 83. When the telescopically movable shield 40 is rotated the two hooks 42 on the telescopically movable shield 40 can be brought into engagement with the two hooks 83 provided on the connector element 80.

Figure 5A:
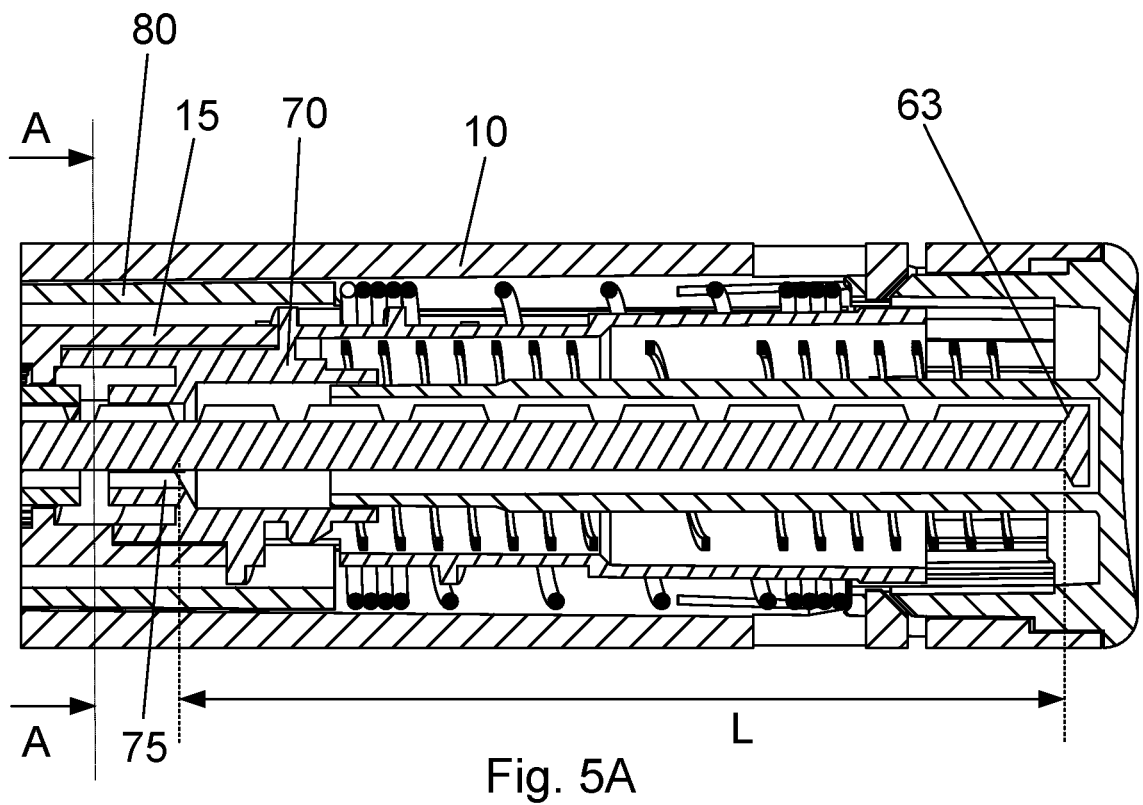
FIG. 5A-B shows a more detailed cross-sectional view of the proximal part of spring driven injection device. The view in FIG. 5B is rotated 90° relatively to FIG. 5A.
Figure 5B:
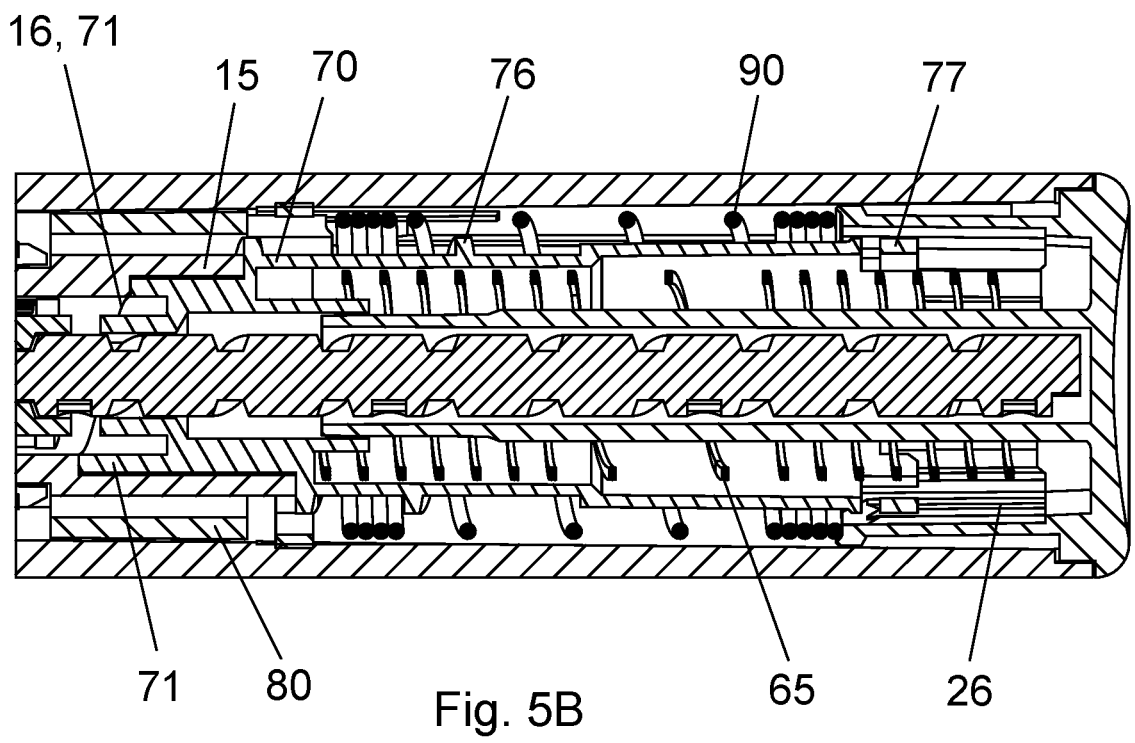

The hooks 83 on the connector element 80 are provided distally on a pair of axially extending parts 84. These axial extending parts 84 makes it possible for the connector part 80 to surround the bridge part 15 of the housing part 10 and operate through the axial openings between the radial bearings 19 in the connection between the bridge part 15 and the housing part 10 as best seen in FIG. 2A, 5A and in FIG. 17A.

Spring Attachment

The torsion spring 65 is as disclosed in FIGS. 2A-B located between the drive tube 70 and the spring base 25 such that the torsion spring 65 is able to rotate the drive tube 70 relatively to the spring base 25 which is a part of the housing structure.

Figure 11A:
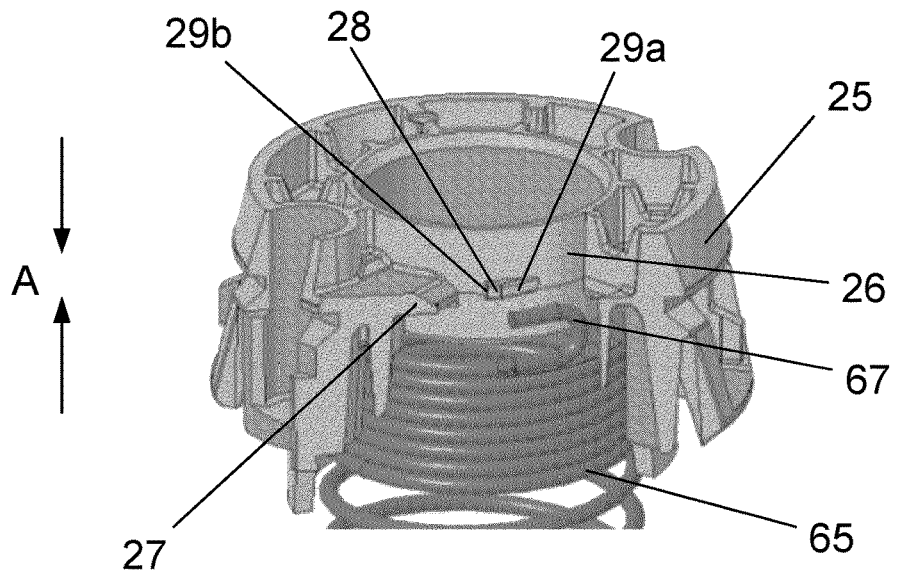
FIG. 11A-C shows the attachment of the torsion spring to the spring base of the housing structure.
Figure 11B:
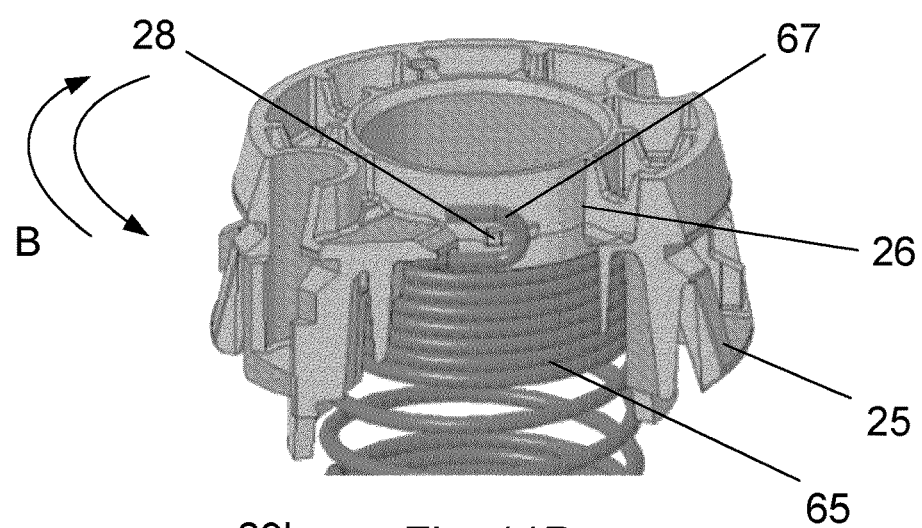
Figure 11:
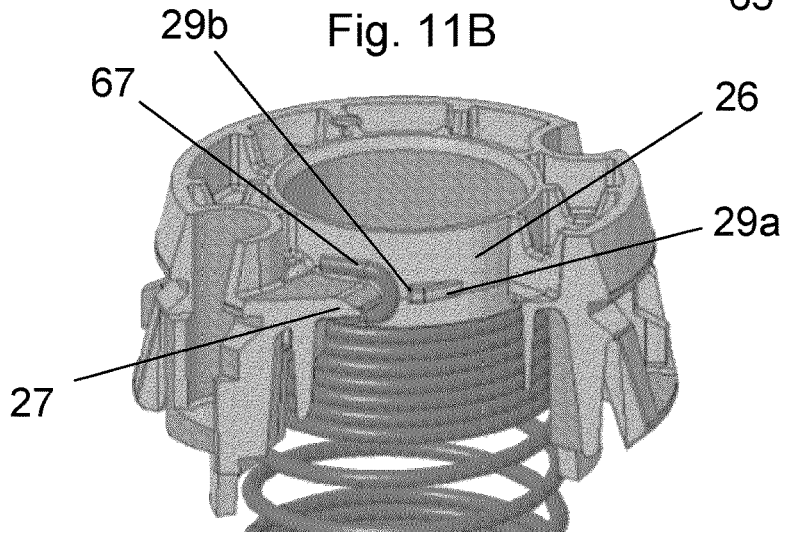
Figure 12:
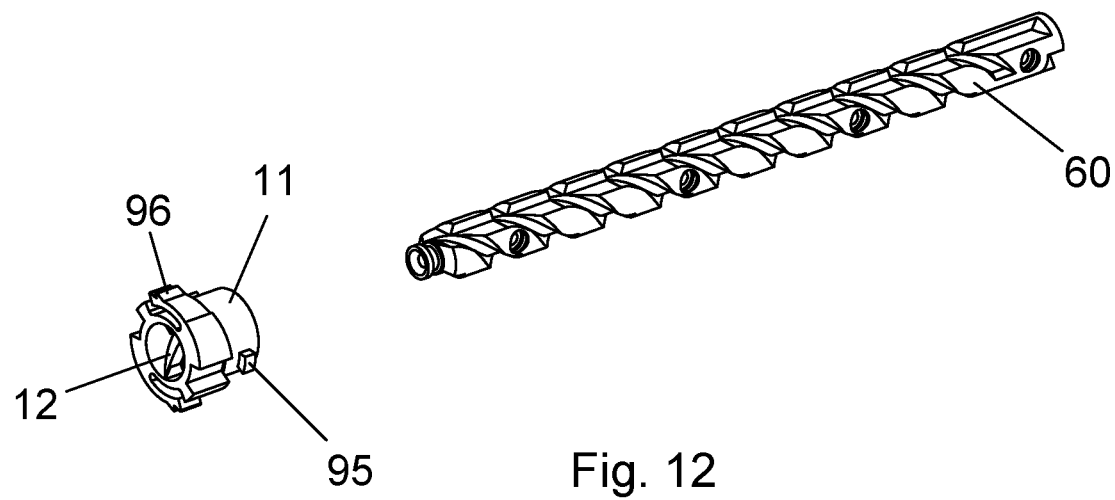
FIG. 12 shows an exploded view of the piston rod and the nut member for zero-point adjustment according to a first example.

In one example disclosed in FIGS. 11A-C, the torsion spring 65 is provided with hooks 67 at the ends of the torsion spring 65. To illustrate the spring attachment, the FIGS. 11A-C only shows the proximal end of the torsion spring 65 and also only a part of an alternative spring base 25. All though, the FIGS. 11A-C only discloses one end of the torsion spring 65, it is clear that both ends can be provided with such hooks 67 and attached in the same manner.

In order to mount the torsion spring 65, one hook 67 is first passed translationally through an axial passage 26 in e.g. the spring base 25. This translational movement is indicated by the arrows "A" in FIG. 11A which indicates that the movement between the spring base 25 and the torsion spring 65 is a relative movement i.e. one or both of the elements can be moved translational.

Once the hook 67 has been passed axially through the axial passage 26 as disclosed in FIG. 11B, the torsion spring 65 and the spring base 25 are rotated relatively to each other such that the hook 67 captures over the shelf 27 formed in the spring base 25 as indicated in FIG. 11C.

In order to irreversible secure the torsion spring 65 to the spring base 25, a radial snap protrusion 28 is located on the spring base 25 in the axial passage 26.

When the torsion spring 65 and the spring base 25 are rotated relatively, the hook 67 of the torsion spring 65 passes over this radial snap protrusion 28 and hence irreversible locks to the spring base 25 as shown in FIG. 11C.

The radial snap protrusion 28 has two sides provided in the rotational direction. The side which first encounters the hook 67 during the rotation has a sloped surface 29a to make it easier for the hook 67 of the torsion spring 65 to slide over the radial snap protrusion 28. The opposite side of the snap protrusion 28 is preferably provided with a steep surface 29b to hinder that the hook 67 of the torsion spring 65 can be rotated in the opposite direction once it has been attached.

In one example, the sloped surface 29a is angled such that the hook 67 of the torsion spring 65 cannot pass by the radial snap protrusion 28 without being forced by an assembly tool. In such example it is not sufficient to just rotate the spring base 25 and the torsion spring 65 relatively. This is especially the case if the torsion spring 65 has open windings such that a sufficient torque cannot be transferred to the proximal end carrying the hook 67 when rotating the torsion spring 65. In such case it is necessary to use an assembly tool which grips the torsion spring 65 at the proximal end and forces the hook 67 to pass the radial protrusion.

The assembly tool can in one example be a support element which enters into the axial passage when the torsion spring 65 is in the position disclosed in FIG. 11B and abuts the hook 67 on the backside to thereby force the hook 67 rotational over the radial snap protrusion 28 and into the position disclosed in FIG. 11C.

All though, the radial snap protrusion 28 is disclosed in connection with the spring base 25, such radial snap protrusion 28 could also be provided on the drive tube 70 to secure the other end of the torsion spring 65. Snap protrusions 28 could henceforth be provided either on the spring base 25 or on the drive tube 70 or on both elements.

In one example, the torsion spring 65 is first attached to the either the spring base 25 or to the drive tube 70 by a purely rotational movement and e.g. by use of a tool. This forms a preassembled unit comprising either the spring base 25 or the drive tube 70 and the torsion spring 65. Since the torsion spring 65 is irreversible attached due to the radial snap protrusion 28, this preassembled unit can be move around in the assembly process without the torsion spring 65 being separated from either the spring base 25 or the drive tube 70.

At a later stage during the assembly process, the torsion spring 65 can be attached to the other part of the spring base 25 or the drive tube 70 also by rotating this part and the torsion spring 65 relatively to each other.

Preferably, the preassembled unit consist of the torsion spring 65 and the drive tube 70. During the preassembling process the torsion spring 65 is irreversible attached to the drive tube 70 as described above. Once this preassembled unit has been positioned inside the housing part 10, the spring base 25 is rotated into engagement with the proximal hook 67 of the torsion spring 65 and axially secured to the housing part 10 by engagement with a pair of flexible coupling arms 9 provided on the housing part 10 (best seen in FIG. 15-16). In one example, the radial snap protrusion 28 is only provided on the drive tube 70 and not on the spring base 25.

Injection

When the telescopically movable shield 40 has been rotated to its unlocked position, the user ejects the predetermined dose volume by pressing the distal shield tip 55 of the telescopically movable shield 40 against the skin whereby the telescopically movable shield 40 moves translational in the proximal direction. This translational movement is transferred to a similar translational movement of the connector element 80.

The connector element 80 which is depicted in further details in FIG. 7A-B is guided translational in relation to the housing part 10 during dosing and the two inwardly pointing protuberances 81, 82 abut the outwardly pointing protuberances 73, 74 on the outer surface of the drive tube 70 such that the drive tube 70 is also moved translational together with the connector element 80. The compression zones 66 on the torsion spring 65 allow the drive tube 70 to be moved translational in the proximal direction and the compression of the torsion spring 65 further apply an axial force onto the drive tube 70 urging the drive tube 70 in the distal direction.

The translational movement of the drive tube 70 in the proximal direction makes the first axial drive flange 72 and the second axial drive flange 78 on the drive tube 70 slide along the first axial housing flange 17 and the second axial housing flange 18 in the housing part 10 respectively. At the same time the inwardly pointing protrusions 75 on the drive tube 70 slides an axial distance in the longitudinal track structure 62 on the piston rod 60.

The size of the predetermined dose volume prepared by this translational movement of the drive tube 70 is henceforth correlated to the longitudinal distance the drive tube 70 is moved i.e. the axial length of the engagement between the first axial drive flange 72, and the first axial housing flange 17 and the axial length of the engagement the second axial drive flange 78 and the second axial housing flange 18 and to the pitch of the threaded connection 12, 61 between the piston rod 60 and the nut member 11. The translational distance the drive tube 70 is moved when the predetermined dose volume is prepared is referred to as "dl" (activation distance).

Once the first axial drive flange 72 and the second axial drive flange 78 has been moved translational out of engagement with the first axial housing flange 17 and the second axial housing flange 18, the torque stored in the torsion spring 65 will force the drive tube 70 to rotate such that the helical shape 71 on the drive tube 70 rotates down the housing helical shape 16 inside the housing part 10 until the first axial drive flange 72 and the second axial drive flange 78 again abut the first axial housing flange 17 and the second axial housing flange 18. The helical movement can be supported by an additional helical interface as previously explained. This rotation is in the disclosed example 360° i.e. the drive tube 70 rotates one full revolution each time it is translated the activation distance "dl" in the proximal direction. The piston rod 60 is henceforth also rotated 360° and thus moved the distance in the distal direction given by the pitch of the thread 61 on the piston rod 60 and the pitch 12 in the engaging nut member 11.

Each of the predetermined dose volumes are thus prepared when moving the drive sleeve 70 the activation distance "dl" translationally in the proximal direction and ejected when rotating the drive sleeve 70 in the distal direction and back to its initial position.

A shield spring 90 in form of a helical coiled compression spring is provided between the connector element 80 and the housing structure, preferably between the connector element 80 and the spring base 25 and applies a compression force onto the connector element 80 when the connector element 80 has been translated proximally during dose preparation. The compression of the shield spring 90 urges the connector element 80 in the distal direction.

As also seen in FIG. 6A-B, the drive tube 70 is on the outer surface provided with a helical flange 76 which engages with the inwardly pointing protuberances 81, 82 inside the connector element 80 when the torsion spring 65 starts to rotate the drive tube 70. This engagement between the inwardly pointing protuberances 81, 82 and the helical flange 76 supports the helically guiding of the drive tube 70.

The helical flange 76 on the drive tube 70 is provided with two axial openings "d" (FIG. 6A-B) through which the inwardly pointing protuberances 81, 82 inside the connector element 80 can slide translational when the openings "d" are rotational aligned with the inwardly pointing protuberances

81, 82. This alignment occurs when the first axial drive flange 72 and the second axial drive flange 78 on the drive tube 70 again are about to abut the first axial housing flange 17 and the second axial housing flange 18 inside the housing part 10 which is when the predetermined dose volume has been expelled. The shield spring 90 will thus push the connector element 80 and the telescopically movable shield 40 in the distal direction once the predetermined dose size has been expelled i.e. after the drive tube 70 has rotated 360° (in the example) and reached its initial position.

Also in this state will the inwardly pointing protuberances 81, 82 align with the outwardly pointing protuberances 73, 74 such that the subsequent next dose volume can be released by repeating the procedure described herein.

When the telescopically movable shield 40 is moved back to its initial position, the cleaning assembly 50 carried by the telescopically movable shield 40 is brought back to its initial position wherein the distal tip of the needle cannula 46 is positioned inside the cleaning chamber 50.

During the movement of the telescopically movable shield 40 in the distal direction, the helical structure 41 on the telescopically movable shield 40 abuts a similar helical path 33 provided inside the housing structure and preferably on the inner surface of the shield guide 30 which forces the telescopically movable shield 40 to rotate into its locked position as the telescopically movable shield 40 is moved back to its initial position.

End-of-Content

Consequently, the predetermined dose volume is prepared by moving the drive tube 70 in the proximal direction by pushing the telescopically movable shield 40 against the skin of the user. When the drive tube 70 is moved the activation distance "dl" in the proximal direction, the first helical shape 71 on the drive tube 70 is brought to its released position wherein the axial drive flanges 72, 78 is released from the axial housing flanges 17, 18. In this released position, the drive tube 70 is able to be rotated under influence of the torque stored in the torsion spring 65. As explained, the drive tube 70 moves helically in the distal direction during its rotation. Also, during this rotation, the drive tube 70 rotates the piston rod 60 due to the engagement between the longitudinal track structure 62 of the piston rod 60 and the inwardly pointing protrusions 75 inside the drive tube 70. Since the piston rod 60 is threaded (61, 12) to the nut member 11 fixed in the housing structure, the piston rod 60 moves helically in the distal direction during rotation.

Every time the drive tube 70 is moved the activation distance "dl" in the proximal direction and released, the piston rod 60 in this embodiment is forced to rotate 360° i.e. one full revolution and thus move forward the axial distance given by the pitch of the thread between the piston rod 60 and the nut member 11. Once the remaining distance between the inwardly pointing protrusions 75 on the drive tube 70 and the stop surface 63 on the piston rod 60 is less than the length "dl" of the axial flanges 72, 78, 17, 18 it is not possible to move the drive tube 70 into its released position to release a further fixed dose.

When the injection device is delivered to the user, the stop surface 63 on the piston rod 60 is located at the proximal end of the injection device as disclosed in FIG. 3. However, for each ejection of a predetermined dose size, the piston rod 60 is moved in the distal direction until the stop surface 63 on the piston rod 60 is in a position in which the drive tube 70 cannot be moved the full activation distance "dl" in the proximal direction. When this occurs, it is not possible to move the drive tube 70 into its released position and it is thus not possible to select a further predetermined dose size which prevents the user from expelling further predetermined doses.

In other words, when the remaining part of the free length "L" of the track structure 62 of the piston rod 60 is shorter than the activation distance "dl", it is not possible to move the axial drive flanges 72, 78 out of engagement with the axial housing flanges 17, 18 and thus release a further of the fixed dose volumes Conclusively, the drive tube 70 is moved translational an activation distance "dl" in the proximal direction every time the user prepares one of the predetermined dose volumes and rotated back to its initial position when the prepared and predetermined dose volume is expelled. In this rotational movement, the drive tube 70 is preferably rotated approximately 360°. Once the accumulated times the drive tube 70 has been moved the activation distance "dl" and the accumulated distance the piston rod 60 has been moved in the distal direction leaves less than the length "dl" of the free length "L" of the track structure 62 of the piston rod 60 available, the stop surface 63 on the piston rod 60 prevents the dose tube 70 from being moved a full fixed dose setting (i.e. a full activation distance "dl") in the proximal direction and thus prevents that the user can select a full predetermined diose size.

In a different embodiment, the first helical shape 71 and the housing helical shape 16 can be divided into more than one surfaces such that more than one axial flange abutments (72, 18; 78; 17) are provided. In such case, the possible rotation of the drive tube 70 and the piston rod 60 for each translational movement can be different from 360°. If e.g. double the number of axial flange abutments were provided, the rotation would be 180° such that the piston rod 60 is only rotated half of a full rotation for each dose release.

Example of End-of-Content

In one example, the free length "L" of the track structure 62 can be e.g. 43 mm i.e. the translational distance between the engagement of the inwardly pointing protrusion 75 of the drive tube 70 with the piston rod 60 and the stop surface 63 in the piston rod 60 is factory set to 43 mm.

In order to release one of the fixed doses, the drive tube 70 is moved the activation distance "dl" in the proximal direction. In the example "dl" can be 5 mm. Once the drive tube 70 has been moved the activation distance "dl"=5 mm in the proximal direction, the torsion spring 65 rotates the drive tube 70 one full revolution (i.e. 360°) back to its initial position. During this rotation, the piston rod 60 is also forced to rotate the same number of degrees i.e. 360°. Depending on the pitch of the threaded connection between the piston rod 60 and the nut member 11, the piston rod 60 is moved a given axial distance in the distal direction for each full revolution. The pitch could e.g. be such that the distance the piston rod 60 is moved is e.g. 10 mm for each full rotation (360°) of the piston rod 60. This means that once four (4) fixed doses has been released (i.e. the drive tube 70 has been moved the activation distance "dl" four times), the piston rod 60 has been moved 40 mm in the distal direction leaving only 3 mm of the free length "L" of the track structure 62 free before the stop surface 63 is reached and since the drive tube 70 require an axial movement of "dl"=5 mm in order to release a further fixed dose volume, it is no longer possible to release further fixed dose volumes all though 3 mm of the free length "L" of the track structure 62 remains.

Zero-Point Adjustment

In one embodiment of the invention primarily disclosed in FIGS. 12 to 17A-B, the nut member 11 can be a separate element which is secured to the housing part 10 of the housing structure during assembly of the injection device. In such embodiment the nut member 11 can be secured in the housing structure without the use of physical attachments means such as gluing or welding. By using a specialized assembly, the nut member 11 can in such embodiment also be used to fully eliminate or at least significantly minimize any air-gap arising from the different tolerances in the assembly process. Such air-gap elimination is also often referred to as zero-point adjustment. The zero-point is meant to be point where the piston rod 60 (or piston rod foot 85) abut the plunger 7 inside the cartridge 5. When such abutment is accomplished during the manufacture of the injection device, the user is not required to perform an initial priming of the injection device before expelling the first dose volume.

Figure 14A:
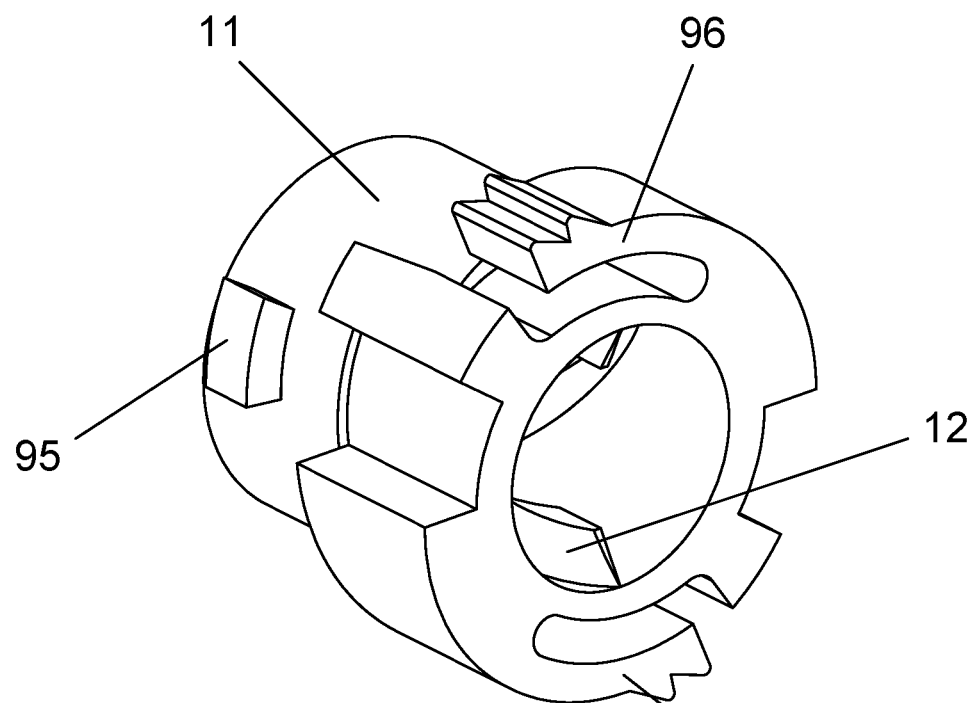
FIG. 14A-B shows a perspective view of the zero-point adjustment nut member viewed from opposite ends.
Figure 14B:
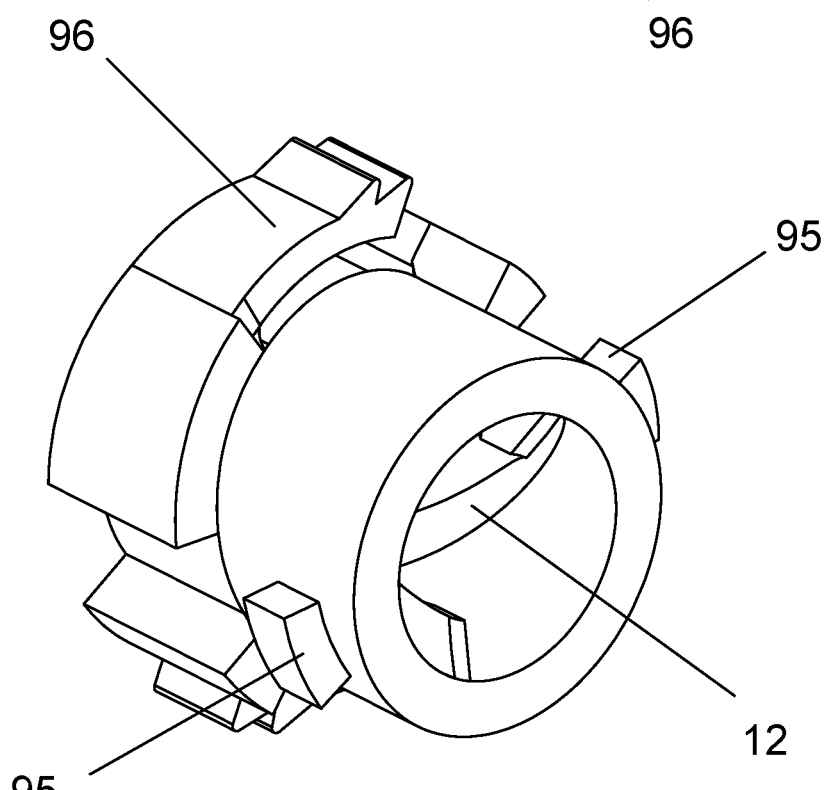

A nut member 11 for this purpose is disclosed in FIG. 14A-B and comprises the internal thread 12 engaging the outer thread 61 on the piston rod 60 and two outer thread protrusions 95 provided proximally on the nut member 11. These two angled thread protrusions 95 together form an outer thread on the nut member 11. However, this outer thread can be made from either one or more flanges or any number of outer thread protrusions 95.

The nut member 11 is further, and also on an outer surface, provided with a number of ratchet arms 96, the use of which will be explained. In the disclosed embodiment, two ratchet arms 96 is disclosed distally on the nut member 11, however any suitable number can be provided.

Figure 16:
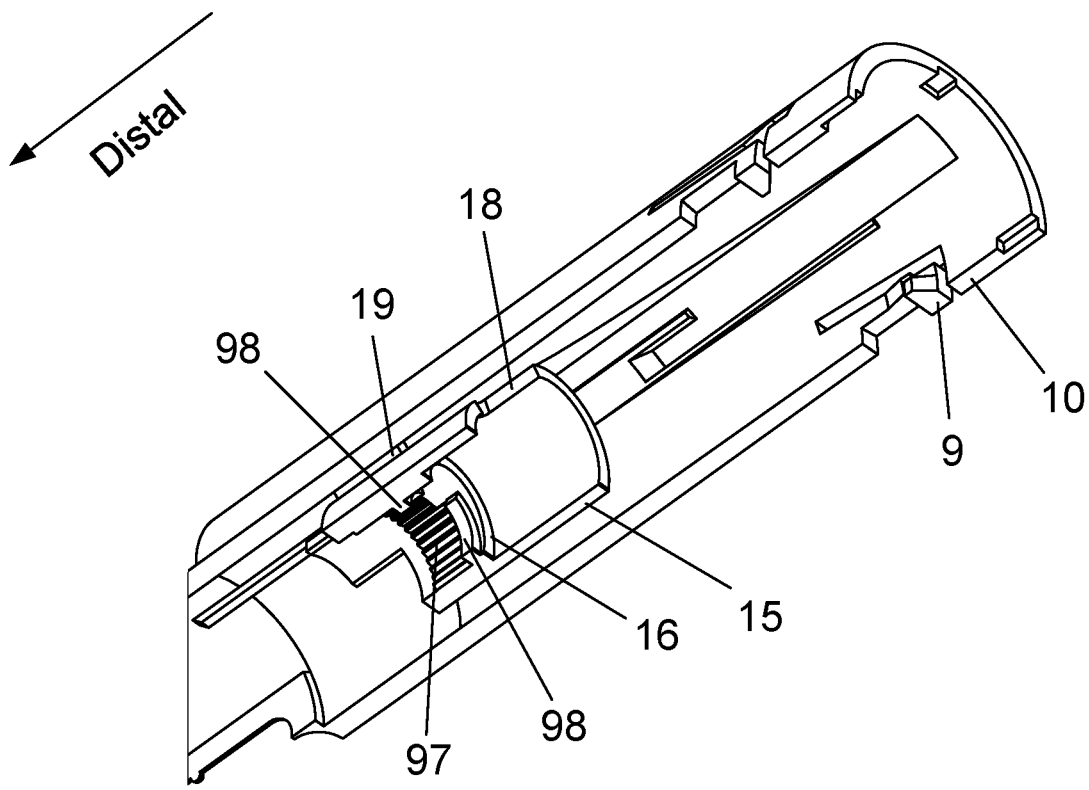
FIG. 16 shows a cut-open part of the housing part for the zero-point adjustment.

The bridge structure 15 inside the housing part 10 as e.g. disclosed in FIG. 16 supporting the nut member 11 is in this example provided with an axial toothing 97 which allows the nut member 11 to rotate in one direction only. The allowed rotational direction being clock-wise; meaning that the ratchet arms 96 and the toothing 97 interface such that rotation in the counter clock-wise direction is prevented.

The bridge structure 15 inside the housing part 10 is further provided with an internal thread 98 having a direction such that the nut member 11 is helically screwed in the proximal direction when rotated in the allowed clock-wise direction.

During assembly of the injection device, one important object is to eliminate the distance—the so-called air-gap—existing between the piston rod 60 and the plunger 7 inside the cartridge 5. If a piston rod foot 85 is attached to the piston rod 60 as disclosed in FIG. 13, the object is to eliminate the physical distance between the distal surface of the piston rod foot 85 and the proximal surface of the plunger 7 such that the piston rod foot 85 and the plunger 7 abut when the injection device is delivered to the end user in an unused state.

When the nut member 11 is rotated relatively to the housing structure during final assembly, the piston rod 60 is advanced in the distal direction until the piston rod 60 or the piston rod plunger 85 abut the plunger 7 inside the cartridge 5.

The rotation of the nut member 11 is preferably done by using a special tool in the production line which are able to engage the nut member 11 and transfer a rotation to the nut member 11. In one preferred example, the piston rod 60 is first located into engagement with the nut member 11 which is located in the bridge structure 15 in the housing part 15. Hereafter, electronic computerized equipment is used to detect the position of the plunger 7 in the cartridge 5 to be used for that specific injection device. When the position of the plunger 7 and the position of the piston rod 60 (or piston rod foot 85) is measured and known, the computer will be able to determine how much the nut member 11 needs to be rotated in order for the piston rod foot 85 or the piston rod 60 in the specific injection device, to be in abutment with the plunger 7 when the injection device is assembled.

The position of the most proximal end of the piston rod 60 or the piston rod foot 85 is thus finetuned by rotating the nut member 11 in the one-way interface with the bridge structure 15. It is here important that the nut member 11 is allowed to rotate in the rotational direction that advances the piston rod 60 (or piston rod foot 85) into contact with the plunger 7.

The piston rod 60 is further provided with an axial track structure 62 which is engaged by the inwardly pointing protrusion 75 on the drive tube 70 which is further provided with a number of ratchet arms 77 engaging a tooting 26 inside the spring base 25 forming a one-way ratchet interface such that the drive tube 70 is only rotational in one direction which in the disclosed example is the counter clock-wise direction when the injection device is viewed from a distal position. These ratchet arms 77 thus prevents rotation of the piston rod 60 in the clock-wise direction.

The engagement between the piston rod 60 and the drive tube 70 henceforth prevents the piston rod 60 from rotation in the clock-wise direction. Consequently, when the nut member 11 is rotated in the clock-wise direction, this rotation is transferred to a translation of the piston rod 60 in the distal direction since the piston rod 60 is unable to follow the clock-wise rotation of the nut member 11.

When a dose is expelled, the drive tube 70 and the piston rod 60 rotates in the counter clock-wise direction. Since the nut member 11 is prevented form rotation in the counter clock-wise direction due to the one-way ratchet interface 96, 97 between the nut member 11 and the housing part 10 (via the bridge structure 15), the nut member 11 does not rotate and thus supports the helical movement of the piston rod 60 in the distal direction.

In order to eliminate the air-gap between the piston rod 11 (or the piston rod foot 85) and the plunger 7 inside the cartridge 5, the nut member 11 is rotated relatively to the housing structure in the clock-wise direction which translate the piston rod 60 in the distal direction.

When the piston rod 11 (or piston rod foot 85) abuts the plunger 7 it is not possible to rotate the nut member 11 further in the clock-wise direction. However, in one example the above is done by electronically measuring the positions before final assembly such that the piston rod foot 85 is in the correct position when assembled with the cartridge holder part 20.

Due to the one-way interface 96, 97 between the nut member 11 and the housing part 10, it is not possible to rotate the nut member 11 in the counter clock-wise direction (when viewed from a distal position)

The result of the above is that the nut member 11 is self-locking in relation to the housing structure and it is not necessary to physically secure the nut member 11 to the housing structure. It is henceforth not necessary to weld or glue the nut member 11 to the housing structure as described in the prior art.

By self-locking is here meant that the nut member 11 cannot rotate in the clock-wise direction since the piston rod 60 (or foot 85) abuts the plunger 7 and the nut member 11 cannot be rotated in the counter clock-wise direction due to the one-way ratchet interface 96, 97.

When the piston rod 60 is rotated in the counter clock-wise direction to expel the prepared dose volume, the nut member 11 is unable to follow this rotation also due to the one-way ratchet interface 96, 97 and when the nut member 11 is rotated clock-wise to eliminate the air gap during assembly, the piston rod 60 is prevented from following this rotation by the engagement (62, 75) with the drive tube 70 and the engagement (77, 26) between the drive tube 70 and the housing structure.

If the pitch of the first threaded connection 61, 12 between the piston rod 60 and the nut member 11 is high i.e. the piston rod 60 moves a long distance for each rotation, it is prudent to have a second threaded connection 95, 98 between the thread protrusions 95 on the nut member 11 and the thread flanges 98 inside the housing part 10 such that the nut member 11 can be screwed helically in the proximal direction relatively to the housing structure during rotation of the nut member 11.

As best seen in FIG. 17B the protrusions 95 making up the outer thread on the nut member 11 is secured behind the thread flanges 98 internally in the bridge structure 15 of the housing part 10 such that the nut member 11 is moved proximally when rotated relatively to the housing structure. Further, it is depicted in FIG. 16 that the thread flange 98 internally in the bridge structure 15 has an axial opening allowing the thread protrusion 95 on the nut member 11 to engage proximally behind the thread flange 98.

This means that when the nut member 11 is rotated in the clock-wise direction, the nut member 11 is moving proximally while it is moving the piston rod 60 in the distal direction. Therefore, the pitch of the second threaded connection 95, 98 between the nut member 11 and the housing structure must be subtracted from the pitch of the first threaded connection 61, 12 between the piston rod 60 and the nut member 11 in order to find the effective zero-point adjustment pitch.

A low effective pitch in the zero-point adjustment makes it easier to finetune the air-gap elimination process. It is thus beneficial to have a second threaded connection 95, 98 between the nut member 11 and the housing part 10 when operating with a piston rod 60 with a high pitch which is the case when a relatively large volume has to be ejected for each rotation of the piston rod 60.

When the pitch of the first threaded connection 61, 12 between the piston rod 60 and the nut member 11 is low, a second threaded connection 95, 98 is not considered necessary and the nut member 11 thus just needs to be rotational in one planar relatively to the housing structure without the ability to move axially.

Alternative Zero-Point Adjustment

An alternative nut member for the zero-point adjustment is disclosed in FIG. 18A to FIG. 19B. This alternative nut member is assigned the reference number 111 and the various elements added in this embodiment are prefixed with a "1" in front. The remaining constructional parts in this embodiment are numbered with the same numbers as used in the previous embodiments.

The nut element 111 is on the inner surface provided with an inner thread 112 and on the outer surface provided with a pair of resilient arms 113. Although, only two resilient arms 113 are disclosed in this embodiment any number of resilient arms 113 can be provided.

The axial opening in the bridge structure 15 of the housing structure which guides the nut element 111 is in this embodiment provided with at least one and preferably two axially extending grooves 115 which guides the resilient arms 113 translational. The engagement between the groves 115 and the flexible arms 113 henceforth secures that the nut element 111 is only able to slide translational i.e. without rotation relatively to the housing structure.

The grooves 115 are provided with a sloped bottom surface 116 (see FIG. 18B) which slopes radially outwardly in the distal direction. This has the effect that the resilient arms 113 are exposed to a growing radial force when moved in the proximal direction and are thus urged in the distal direction with an increased force the further proximally the nut element 111 is moved.

As seen in the figures, the flexible arms 113 preferably slopes in the radial direction such that the flexible arms 113 follows an angle relatively to the centre axis corresponding to the angle of the sloped bottom surface 116.

To assemble the injection device, the nut element 111 and the piston rod 60 are first pre-assembled by rotating the nut element 111 and the piston rod 60 relatively to each other such that the nut element 111 is threaded onto the piston rod 60. The pre-assembled piston rod 60 and nut element 111 are hereafter placed inside the opening in the bridge structure 15 as disclosed in FIG. 18A.

Figure 18A:
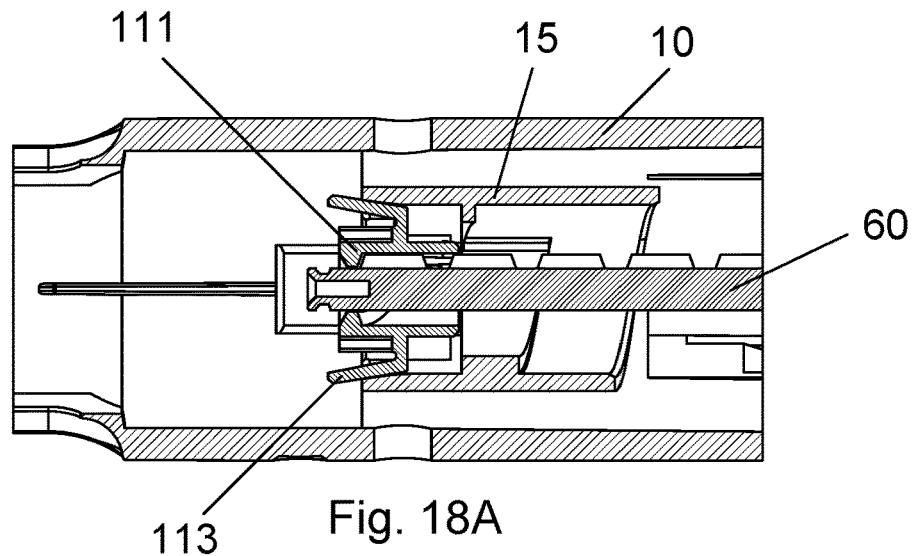
FIG. 18A-C shows a cross-sectional view of an alternative zero-point adjustment.
Figure 18B:
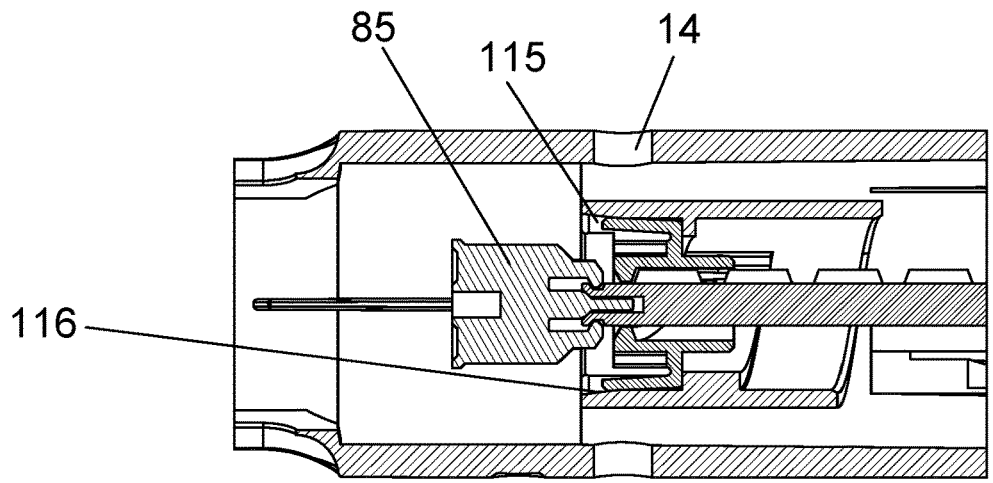
Figure 18C:
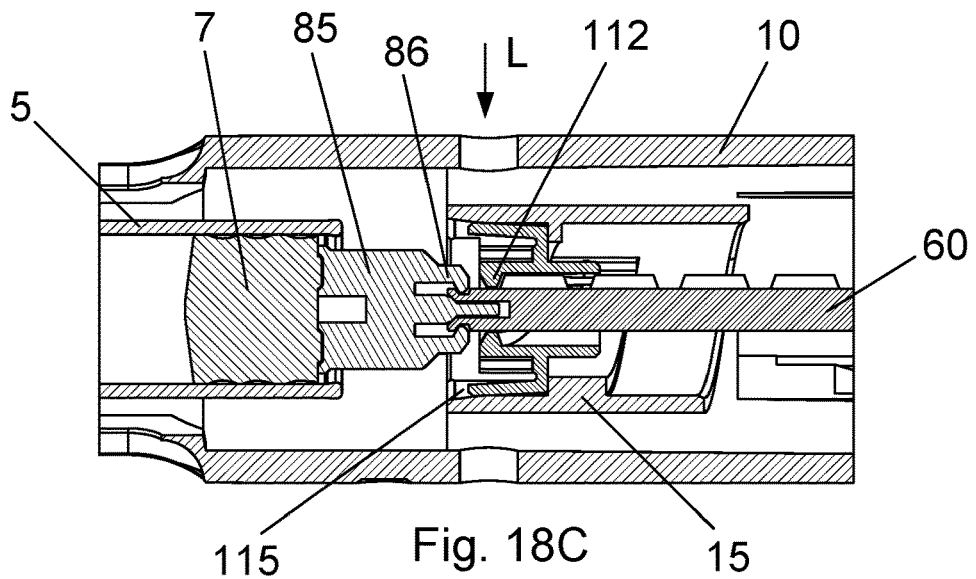
Figure 19A:
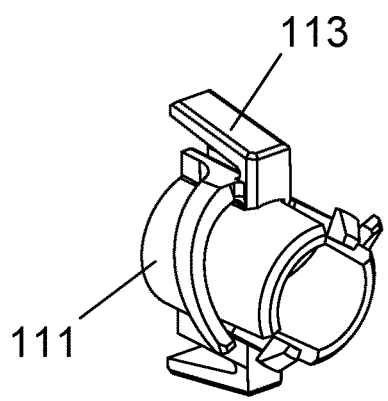
FIG. 19 shows the nut member for the alternative solution shown in FIG. 18A-C.
Figure 19B:
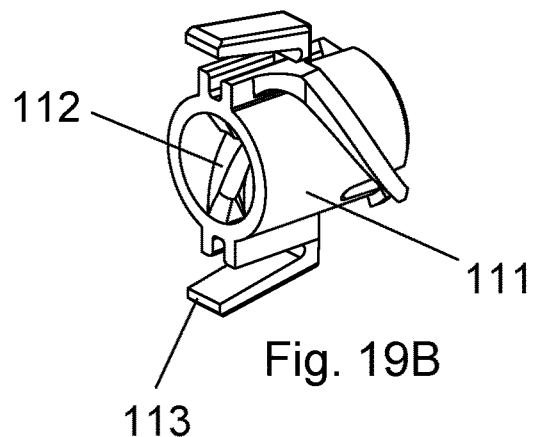

When the injection device is fully assembled, the piston rod 60 can abut directly with the plunger 7 inside the cartridge 5 or a piston rod foot 85 can be provided between the piston rod 60 and the plunger 5 such that the abutment lies between the piston rod foot 85 and the plunger 7 as disclosed in FIG. 18C.

In one example, this piston rod foot 85 can be connected to the piston rod 60 either before the piston rod 60 is pre-assembled with the nut element 111, simultaneously therewith or after the piston rod 60 has been pre-assembled with the nut element 111 as indicated in FIG. 18B.

The piston rod foot 85 can in one example be click-fitted onto the piston rod 60 in a bearing-like connection such that the piston rod foot 85 is able to rotate relativity to the piston rod 60. In another example, the piston rod foot 85 is a separate or loose element positioned between the piston rod 60 and the plunger 7. Alternatively, the piston rod foot 85 can be rotationally connected to the piston rod 60 to rotate together with the piston rod 60.

In the latter example, the piston rod foot 85 can contain an electronic sensor which is able to register the number of rotations of the piston rod 60 relatively to the cartridge 5 and henceforth the housing structure in order to determine the expelled volume.

Once the piston rod 60 and the nut element 111 are pre-assembled with or without the piston rod foot 85, the nut element 111 is slided axially such that the flexible arms 113 engage the grooves 115 provided in the opening of the bridge section 15 of the housing structure.

In the final step of the assembly, the cartridge 5 is placed inside the cartridge holder 20 and the cartridge holder 20 together with the cartridge 5 is moved in the proximal direction such that the plunger 7 inside the cartridge 5 obtains contact with the piston rod 60 (or foot 85) and the cartridge holder 20 clicks onto the housing part 10 of the housing structure.

Consequently, the plunger 7 inside the cartridge 5 abut the piston rod 60 (or the foot 85) which forces the nut element 111 to slide translationally in the proximal direction. The resiliency in the flexible arm 113 will automatically when the flexible arms 113 pushes against the sloped bottom surface 116 of the grooves 99 urge the nut element 111 and thus the piston rod 60 in the distal direction such that the contact between the plunger 7 and the piston rod 60 (or foot 85) is maintained. Whenever contact between the plunger 7 and the piston rod 60 (or foot 85) is obtained and maintained, a laser beam (indicated with an "L" in FIG. 18C) is directed through an opening 14 in the housing structure and onto the outer surface of the bridge structure 15. As disclosed in FIG. 18C, there can be two such openings 14 or more if required.

The bridge structure 15 is preferably moulded from a polymer which is more transparent to the laser light than the polymer from which flexible arms 113 of the nut element 111 are moulded such that the energy in the laser beam is transformed to heat in the contact surface area between the bridge structure 15 and the flexible arms 113 i.e. on the inner surface of the bridge structure 15.

The injection device according to this embodiment thus has a nut element 111 which can operate between two different states. A first state wherein the nut element 111 is axially movable and wherein the nut element 111 is preferably moved slightly in the proximal direction by impact with the plunger 7 in the cartridge 5. During this axial movement in the proximal direction, the resiliency of the nut element 111 bounces back the nut element 111 in the distal direction thereby maintaining physical contact with the plunger 7.

In the position wherein physical contact between the plunger 7 and the piston rod 60 (or foot 85) is realized, the nut element 111 is welded, or otherwise connected, to the housing structure which henceforth defines the second state of the nut element 111.

In this second state the nut element 111 is axially secured to the housing structure and the piston rod 60 is hereafter moved helically when rotated relatively to the nut element 111 and to the housing structure.

The positioning of the pre-assembled nut element 111 and the piston rod 60 can alternatively be determined electronically such that the welding can be done before the cartridge is actually positioned.

Second Alternative Zero-Point Adjustment

The FIGS. 20 to 22B discloses an alternative solution wherein a telescopic element 100 is disposed between the piston rod foot 85 and the piston rod 60.

Figure 20:
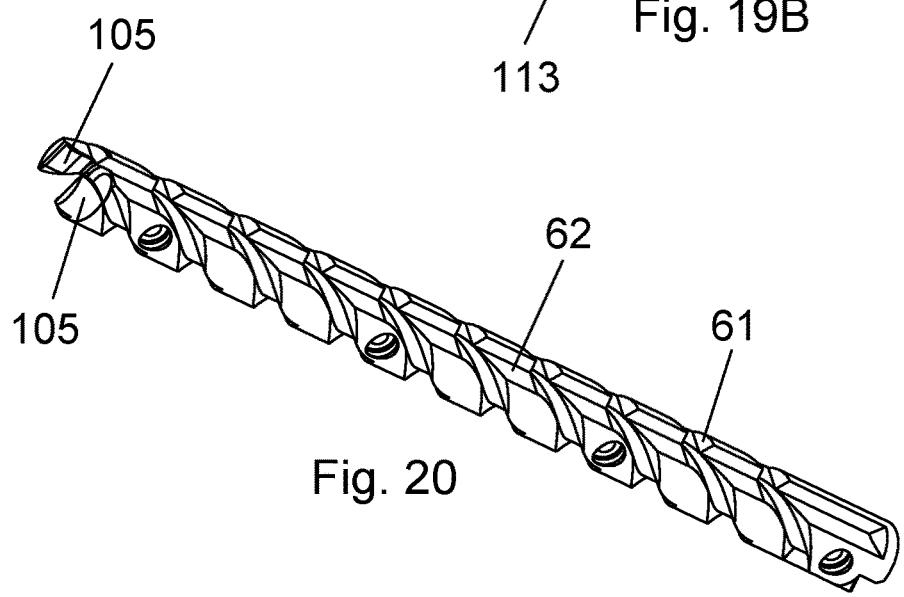
FIG. 20 shows an alternative piston rod for a second alternative zero-point adjustment.

The alternative piston rod 60 is disclosed in FIG. 20 and is distally provided with two claws 105 which are able to grip around the telescopic element 100. All though only two such claws 105 is disclosed any number of claws 105 can be provided.

The piston rod 60 is provided with an outer thread 61 which engages with an inner thread 12 provided in the nut member 11 which in this alternative embodiment preferably is an integrated part of the housing structure. The piston rod 60 is further provided with a longitudinal track structure 62 which is engaged by the drive element 70.

Figure 21:
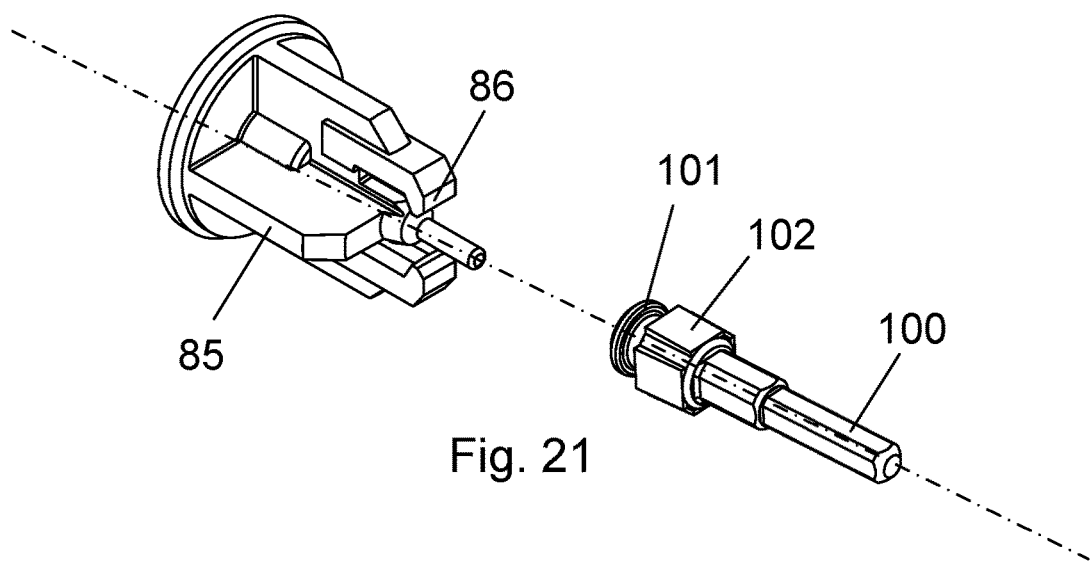
FIG. 21 shows a telescopic connection between the piston rod and the piston rod foot for the second alternative zero-point adjustment.

The telescopic element 100 which is shown in greater details in FIG. 21 is distally provided with a circular rib 101 behind which click arms 86 provided on the piston rod foot 85 engages such that the telescopic element 100 can be axially fixed to the piston rod foot 85. Due to this click-fit connection, the piston rod foot 85 is able to rotate relatively to the telescopic element 100.

Figure 22A:
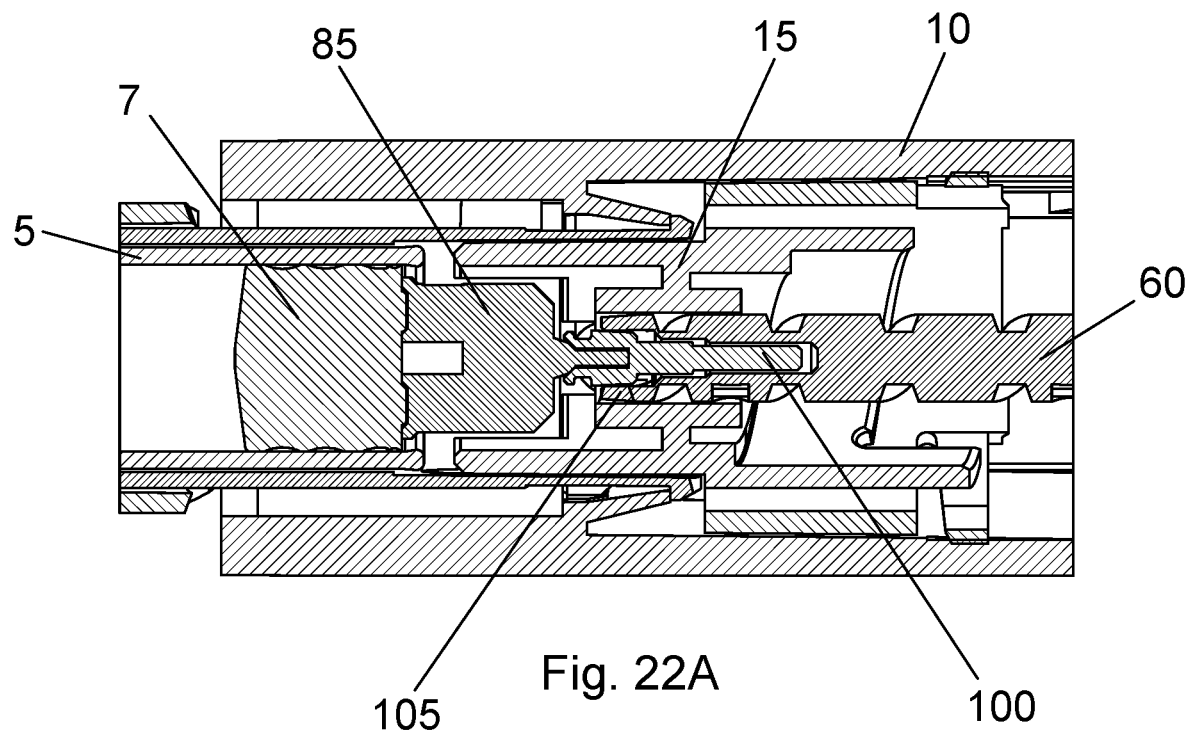
FIG. 22A-B shows a cross sectional view of the second alternative zero-point adjustment. The view in FIG. 22B is rotated 90° relatively to FIG. 22A.
Figure 22B:
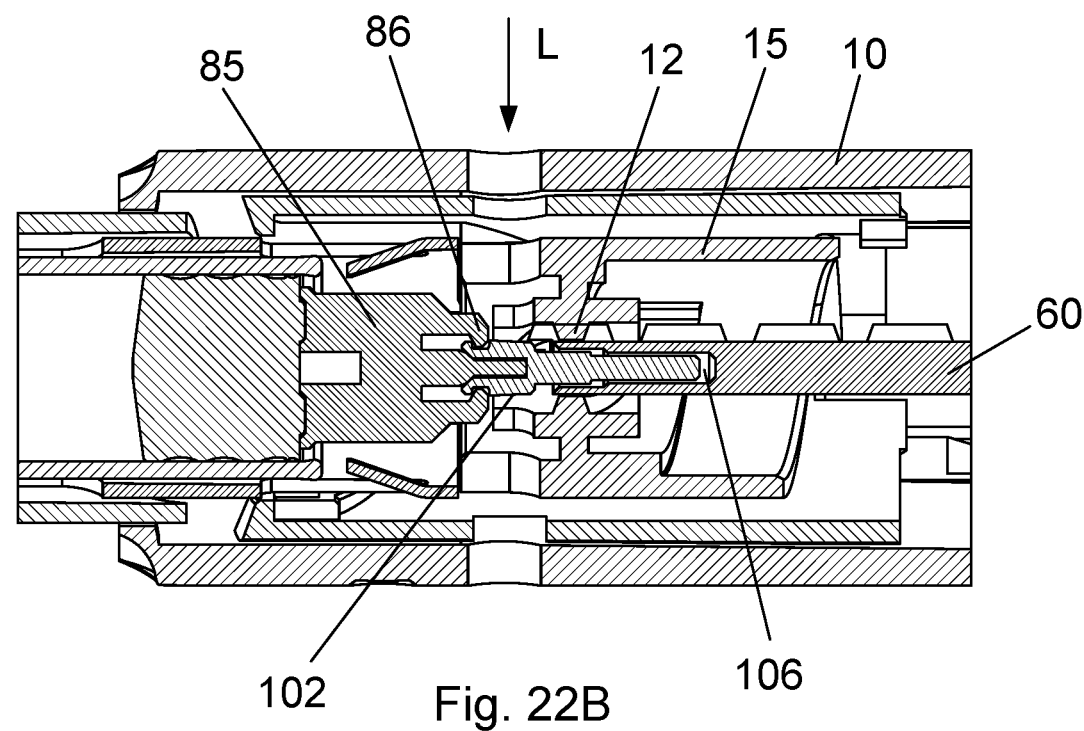

The telescopic element 100 is further provided with a number of outwardly pointing surfaces 102 on which the claws 105 are able to abut as disclosed in FIG. 22A-B. The claws 105 are henceforth suitable of sliding on theses outwardly pointing surfaces 102 such that the telescopic element 100 can slide relatively to the piston rod 60.

The telescopic element 100 is for this purpose slidable arranged in an axial opening 106 in the piston rod 60 such that the piston rod foot 85 together with the telescopic element 100 can slide axially in relation to the piston rod 60.

Once the piston rod foot 85 (connected to the telescopic element 100) has been slided into contact with the plunger 7 inside the cartridge 5 as disclosed in FIG. 22A-B, the telescopic element 100 is welded to the piston rod 60 by pointing a laser beam "L" through the opening 14 in the housing structure and onto the claws 105 of the piston rod 60 which are thus welded to the outwardly pointing surfaces 102 of to the telescopic element 100.

The telescopic element 100 is preferably square-shaped such that four outer surfaces 102 are present and the axial opening 106 are preferably also square-shaped such that the telescopic element 100 can only translate relatively to the piston rod 60 in the first state.

Some preferred embodiments have been shown in the foregoing, but it should be stressed that the invention is not limited to these but may be embodied in other ways within the subject matter defined in the following claims.

The invention claimed is:

1. A pre-filled injection device for delivering liquid drug, comprising:
    a housing structure permanently securing a cartridge having a movable plunger,
    a piston rod for advancing the movable plunger during dispensing, the piston rod having an outer thread and a longitudinal track structure,
    a rotatable drive element engaging the longitudinal track structure of the piston rod, such that rotation of the drive element is transferred to a rotation of the piston rod,
    a nut element having a first thread engaging the outer thread of the piston rod, such that the piston rod is moved helically when rotated relatively to the nut element during dispensing, and
    wherein the piston rod is only allowed rotation in a first rotational direction relatively to the nut element, the allowed first rotational direction being the one that helically advances the piston rod in the dispensing direction,
    wherein the nut element is rotatably coupled to the housing structure in a coupling provided with a one-way ratchet interface only allowing the nut element to be rotated in a second rotational direction opposite the first rotational direction.

2. The injection device according to claim 1, wherein the one-way ratchet interface which rotatably couples the nut element to the housing structure comprises one or more flexible ratchet arms engaging a toothed surface.

3. The injection device according to claim 2, wherein the nut element comprises the one or more flexible ratchet arms.

4. The injection device according to claim 2, wherein the housing structure comprises the toothed surface.

5. The injection device according to claim 1, wherein when the piston rod is maintained in-rotatable, rotation of the nut element in the second rotational direction translates the piston rod in the dispensing direction.

6. The injection device according to claim 1, wherein the rotatable drive element is only rotatable in the first rotational direction.

7. The injection device according to claim 1, wherein the nut element is provided with a thread on an outer surface engaging a thread provided internally in the housing structure.

8. The injection device according to claim 1, wherein the housing structure comprises at least a housing part internally supporting a bridge structure preferably moulded on an inner surface of the housing part.

9. The injection device according to claim 8, wherein the bridge structure is carried on an inner surface of the housing structure by a plurality of radial bearings.

10. The injection device according to claim 9, wherein the toothed surface is provided on an inner surface of a circular opening in the bridge structure.

11. A method of eliminating a distance between a piston rod and a plunger when assembling a pre-filled injection device, wherein
- a nut element is coupled to a housing structure of an injection device,
- a cartridge comprising a plunger is secured in the housing structure,
- the piston rod being able to be advanced in an expelling direction upon rotation of the piston rod relatively to the nut element in a first rotational direction,
- wherein the nut element is rotationally coupled to the housing structure by a one-way ratchet interface allowing the nut element to rotate in a second rotational direction opposite the first rotational direction, the method comprising the steps of:
- securing the piston rod against rotation in the second rotational direction,
- rotating the nut element relatively to the housing structure in the second rotational direction translating the piston rod towards the plunger.

* * * * *